(12) United States Patent
Karpf

(10) Patent No.: US 9,173,900 B2
(45) Date of Patent: Nov. 3, 2015

(54) COMPOSITIONS COMPRISING ELEMENTAL METALS

(75) Inventor: Gary Karpf, Princeton, NJ (US)

(73) Assignee: Prezacor, Inc., Princeton, NJ (US)

( * ) Notice: Subject to any disclaimer, the term of this patent is extended or adjusted under 35 U.S.C. 154(b) by 1748 days.

(21) Appl. No.: 11/921,477

(22) PCT Filed: Jun. 5, 2006

(86) PCT No.: PCT/US2006/021823
§ 371 (c)(1),
(2), (4) Date: Oct. 9, 2009

(87) PCT Pub. No.: WO2006/133134
PCT Pub. Date: Dec. 14, 2006

(65) Prior Publication Data
US 2011/0117179 A1    May 19, 2011

Related U.S. Application Data

(60) Provisional application No. 60/687,179, filed on Jun. 3, 2005.

(51) Int. Cl.
| | | |
|---|---|---|
| A61K 9/14 | (2006.01) | |
| A61K 33/24 | (2006.01) | |
| A01N 25/26 | (2006.01) | |
| A61K 9/00 | (2006.01) | |
| A61K 9/16 | (2006.01) | |
| A61K 9/70 | (2006.01) | |
| A61K 33/26 | (2006.01) | |
| A61K 33/30 | (2006.01) | |
| A61K 33/34 | (2006.01) | |
| A61L 15/18 | (2006.01) | |
| A61L 15/44 | (2006.01) | |
| A61K 9/51 | (2006.01) | |

(52) U.S. Cl.
CPC ............... *A61K 33/24* (2013.01); *A01N 25/26* (2013.01); *A61K 9/0014* (2013.01); *A61K 9/1617* (2013.01); *A61K 9/7023* (2013.01); *A61K 33/26* (2013.01); *A61K 33/30* (2013.01); *A61K 33/34* (2013.01); *A61L 15/18* (2013.01); *A61L 15/44* (2013.01); *A61K 9/5123* (2013.01); *A61L 2300/102* (2013.01); *A61L 2300/41* (2013.01); *A61L 2300/624* (2013.01)

(58) Field of Classification Search
CPC ... A61K 2300/00; A61K 33/00; A61K 47/02; A61K 9/5115; A61K 9/5192
USPC .................. 424/420, 421, 485, 502
See application file for complete search history.

(56) References Cited

U.S. PATENT DOCUMENTS

| | | | |
|---|---|---|---|
| 3,791,801 A * | 2/1974 | Ariga et al. ................... 428/639 |
| 4,123,511 A | 10/1978 | Heintze | |
| 4,454,118 A | 6/1984 | Johnson | |
| 4,706,672 A * | 11/1987 | Jones ............................. 607/112 |
| 4,891,394 A | 1/1990 | Savin | |
| 5,144,529 A * | 9/1992 | Takahashi ...................... 361/323 |
| 5,148,862 A * | 9/1992 | Hashiura et al. ........... 165/134.1 |
| 5,182,171 A * | 1/1993 | Aoyama et al. ............... 428/623 |
| 6,017,553 A | 1/2000 | Burrell et al. | |
| 6,171,606 B1 | 1/2001 | Lyons | |
| 6,264,681 B1 * | 7/2001 | Usui .............................. 607/111 |
| 6,533,963 B1 * | 3/2003 | Schleifstein et al. ......... 252/511 |
| 6,884,314 B2 * | 4/2005 | Cross et al. ................... 156/329 |
| 2004/0135997 A1 | 7/2004 | Chan et al. | |
| 2004/0210289 A1 * | 10/2004 | Wang et al. ................... 607/116 |

FOREIGN PATENT DOCUMENTS

| | | |
|---|---|---|
| CN | 1486726 A | 4/2004 |
| DE | 1947222 A1 | 4/1971 |
| EP | 0 928 611 A1 | 7/1999 |
| GB | 03711 A | 0/1907 |
| GB | 309 394 A | 4/1929 |
| GB | 981372 A | 1/1965 |
| GB | 2307862 A | 6/1997 |
| JP | 58222011 A | 12/1983 |
| JP | 2-275823 | 11/1990 |
| JP | 4-2365 | 1/1992 |
| JP | 6-9363 | 1/1994 |
| JP | 7-16301 | 1/1995 |
| JP | 07-059867 | 3/1995 |
| JP | 2003-137731 A | 5/2003 |
| JP | 2004-035440 A | 2/2004 |
| RU | 2123329 C1 | 12/1998 |
| WO | WO 97/20549 A1 | 6/1977 |
| WO | WO 01/47502 A1 | 7/2001 |
| WO | WO 2005/023206 A2 | 3/2005 |
| WO | WO 2005/023213 A1 | 3/2005 |
| WO | WO 2005/023361 A2 | 3/2005 |

* cited by examiner

*Primary Examiner* — Johann R Richter
*Assistant Examiner* — Danielle Sullivan
(74) *Attorney, Agent, or Firm* — Stradley Ronon Stevens & Young, LLP

(57) ABSTRACT

The invention provides compositions and devices for altering biological field effects and methods for their use in therapeutic and agricultural applications. In particular, the invention provides compositions including one or more elemental metals coated with one or more non-conducting or semi-conducting materials and methods for their application to animals (including humans) and/or plants.

34 Claims, 1 Drawing Sheet

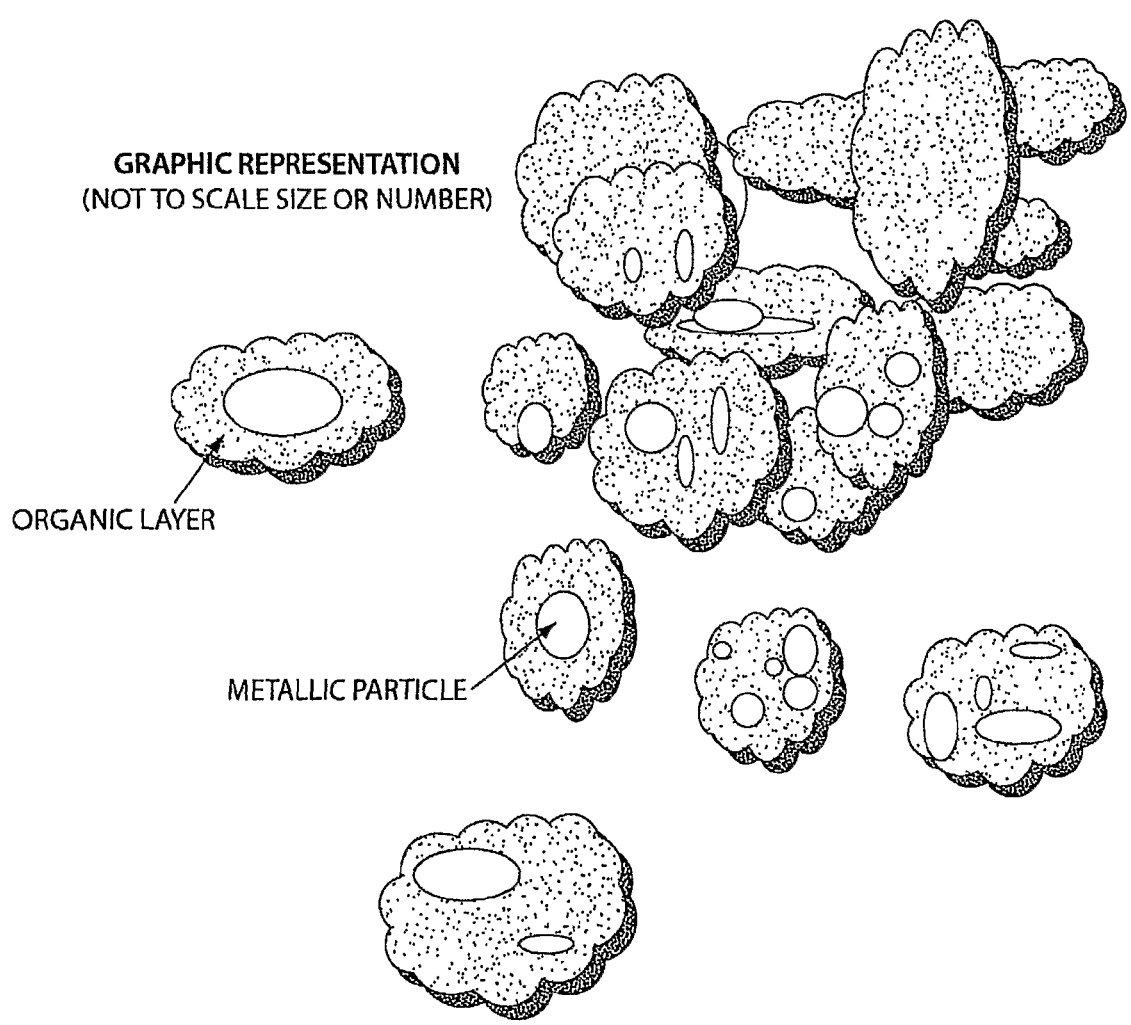

COMPOSITIONS COMPRISING ELEMENTAL METALS

RELATED APPLICATIONS

This application is a national stage filing under 35 U.S.C. §371 of PCT International application PCT/US2006/021823, filed Jun. 5, 2006, which claims priority under 35 U.S.C. §119(e) from U.S. provisional application Ser. No. 60/687,179 filed Jun. 3, 2005, the entire content of which is incorporated by reference herein.

FIELD OF THE INVENTION

Aspects of the invention relate to topical compositions that affect biological processes. In particular, aspects of the invention relate to topical compositions for treating injuries, diseases, and pain in animals including humans. Aspects of the invention also relate to topical compositions that modify certain features of plant physiology.

BACKGROUND

Creams and ointments containing certain metals have been used on humans and other animals as protective materials (e.g., sun creams) and for treating a variety of ailments (e.g., rashes and infections). Examples include creams containing copper sulfate.

SUMMARY

Aspects of the invention provide compositions comprising one or more elemental metals and methods of their use for impacting biological processes in animals and/or plants. Aspects of the invention are based, in part, on the discovery that certain configurations of elemental metals have surprising effects on many biological processes. In particular, compositions comprising one or more elemental metal structures that are mixed and/or coated with one or more non-conducting and/or semi-conducting materials may have significant therapeutic and/or agricultural uses. According to aspects of the invention, certain elemental metal compositions may interact with electrical fields (e.g., electrostatic and/or electromagnetic fields) associated with living biological systems (e.g., cells, tissue, organs, organisms, etc.) and this interaction can be used to alter certain biological processes. In contrast to compositions that deliver metal ions for direct chemical interactions with biological processes and molecules, aspects of the present invention provide compositions with electrostatic and/or electromagnetic properties that may impact a biological system indirectly through electrostatic and/or electromagnetic field effects that do not require direct contact with the biological system. Accordingly, although compositions of the invention may be applied to a biological surface (e.g., skin) in the form of a cream or ointment, compositions of the invention also may be effective when put in close proximity with a biological surface (e.g., the composition may be in an enclosure or container that is placed on or near a biological system).

In one aspect, compositions of the invention include a plurality of conducting elemental metal particles (e.g., balls, beads, powder, nanoparticles, etc.) that are separated from each other by a matrix of non-conducting or semi-conducting material. In one embodiment, the separating matrix material may be in the form of solid particles that are mixed with the elemental metal particles (e.g., in the form of a dry mixture). In another embodiment, the separating matrix material may be in the form of a coating that can be mixed with or applied to the elemental metal particles. The coating may be mixed or applied in a viscous, liquid, or aerosol form. It should be appreciated that a matrix may include a combination of solid particles and coating(s). The resulting composition may be a dry, viscous, or wet composition depending on the intended use. For example, the composition may be a solid, liquid, grainy, semi-solid, waxy, oily, or watery composition comprising elemental metal particles at least some of which are separated from each other by a matrix of non-conducting and/or semi-conducting material. According to one aspect of the invention, the separation of the conducting elemental metal particles produces certain electrical (e.g., electrochemical) properties that can interact with living biological systems and alter the nature and/or magnitude (e.g., intensity, speed, etc.) of certain biological processes. It should be appreciated that the nature, dimensions, and relative amounts of the elemental metal and the matrix materials may alter the electrical properties of a composition and may be optimized for a particular biological application.

Accordingly, one aspect of the invention provides a biologically active elemental metal composition including one or more elemental metal particles within a matrix of non-conducting or semi-conducting material. In one embodiment, the matrix may be a coating material that is disposed around at least a fraction of the surface area of the particulate elemental metal(s). In one embodiment, the matrix may be a particulate material that is mixed with the elemental metal particles and that separates at least a fraction of the elemental metal particles from each other. For example, the material may be a semi-conducting material. The matrix material may be a silicon dust, sulfur, boron, fiberglass, or other suitable material.

In another aspect, the invention provides a solid biologically active elemental metal composition including elemental metal volumes dispersed within a solid matrix of non-conducting and/or semi-conducting material.

Aspects of the invention include using one or more elemental metal compositions to impact one or more biological processes. An elemental metal composition may be used in an amount and for a time sufficient to obtain a particular biological outcome. Biological applications include medical, veterinary, and agricultural applications as described herein. It should be appreciated that different amounts and or exposure times may be appropriate for different applications. Effective and/or optimal compositions and exposure conditions (including amount and/or time of exposure) may be determined for any particular application based on the description and examples provided herein.

In some embodiments, the invention provides a body surface (external) appliance or device constructed to fit a certain body part and containing a compound that is specifically formulated to consist of microscopic capacitors that respond to and resonate with naturally occurring electrical fields (e.g., fields of nerve and/or body tissue).

Accordingly, aspects of the invention may include non-invasive methods, compositions, and devices, for reducing the severity of pain/inflammation/irritation, delaying the onset of pain/inflammation/irritation, reducing the duration of pain/inflammation/irritation, maintaining or increasing mobility, reducing or preventing the use of topical creams or other medication (e.g., pain killers, anti-inflammatory medications, etc., or any combination thereof), increasing the quality of life (e.g., activity and/or mobility) of a patient, and/or delaying or postponing an invasive surgical procedure (e.g., for pain remediation).

BRIEF DESCRIPTION OF THE DRAWINGS

FIG. 1 illustrates a composition including elemental metal particles within a matrix of non-conducting or semi-conducting material (the composition as shown includes air pockets, however, in other embodiments a composition may have few or no air pockets).

DETAILED DESCRIPTION

Aspects of the invention relate to metal containing compositions and devices that impact biological processes. Aspects of the invention are based, in part, on the discovery that certain compositions including one or more elemental metals can be used to alter biological processes by exposing a biological tissue to the composition(s). The invention provides, in part, biologically active compositions including one or more elemental metals referred to herein as elemental metal compositions. In certain aspects, the elemental metal(s) are provided in particulate form. In certain aspects, the elemental metal(s) may be coated with one or more non-conducting or semi-conducting materials. In one aspect, elemental metal compositions of the invention may act as capacitors. In one aspect, elemental metal compositions may have a field effect (e.g., an electrostatic field effect and/or an electromagnetic field effect) on biological tissue. In one aspect, elemental metal compositions may stabilize a biological process when exposed to a biological tissue (e.g., through surface exposure). In one aspect, elemental metal compositions may alter a biological process when exposed to a biological tissue (e.g., through surface exposure).

Certain aspects of the invention include elemental metal particles that are contained within a matrix such that the particles (or a fraction thereof) are separated from each other by the matrix material. In one aspect, the matrix includes one or more non-metallic coating materials (e.g., materials that can form a coating or film on the surface of the elemental metal particles) to enhance the biological effects of the composition. In another aspect, the matrix includes one or more particulate materials (e.g., powders, grains, etc.) that can be mixed with the elemental metals to enhance the biological effects of the composition. A coating and/or particulate matrix material may be less conducting than an elemental metal particle (e.g., a matrix coating or particle may be non-conducting or semi-conducting). Accordingly, a composition of the invention may have non-uniform conductivity that contributes to its capacitor and/or field effect properties. The size of the elemental metal particles may affect the capacitor and/or field effect properties of a biologically effective composition. The average distance between elemental metal particles in the composition also may affect the capacitor and/or field effect properties of a biologically effective composition. In one embodiment, a composition containing smaller elemental metal particles has a greater area of surface contact between the elemental metal(s) and the matrix material(s) resulting in stronger capacitor and/or field effects. It should be appreciated that the capacitor and/or field effects of an elemental metal composition also may be affected by the type of elemental metal(s) and matrix material(s) that are used. In addition, the presence of moisture and/or oxidized metals also may affect (e.g., reduce) the capacitor and/or field effects. Accordingly, a matrix material (e.g., coating) also may be used to exclude moisture (e.g., water) and/or protect the elemental metal(s) from oxidation.

Compositions of the invention may be used to impact physiological processes in animals (e.g., humans) and/or plants. Accordingly, compositions including elemental metals may be used for therapeutic purposes to treat certain conditions in humans and/or other animals. In other embodiments, compositions including elemental metals may be used for agricultural purposes to promote or stabilize certain physiological states in plants.

In one aspect, compositions of the invention may be provided in the form of a topical preparation that can be applied to or contacted to a biological surface (e.g., skin of an animal or surface of a plant). In certain aspects, compositions of the invention may be provided in a container that is adapted to be exposed or contacted to a biological surface (e.g., without the surface being directly contacted by the elemental metal composition). In one embodiment, the elemental metal composition may be formed (e.g., molded) into a solid device having a defined shape (e.g., a shape adapted for contact with a biological surface). In another embodiment, one or more elemental metal(s) may be provided in particulate form and contained within a device. For example, the elemental metal(s) may be provided in a matrix or in a container/sheath. In one embodiment, the elemental metal(s) may form a single solid structure. In another embodiment, the elemental metal(s) may be in the form of two or more structures having similar or different shapes. In one embodiment, the elemental metal(s) are particulate (e.g., balls, filings, grains, granules, nanoparticles, etc.). The particles all may be of approximately the same size. Alternatively, the particles may range in size. The average size of an elemental metal particles may be smaller or larger than the average size of a matrix particle (e.g., the ratio of elemental metal to matrix particle may be between 1/100 and 100/1, for example between 1/10 and 10/1). However, higher, lower, or intermediate ratios may be used. Similarly, the ratio of elemental metal (e.g., by weight or volume) to matrix material (particulate or not) may be between about 1/100 and 100/1 (e.g., between 1/10 and 10/1, about 1/5 to 5/1, or about 1/2 to 2/1, or about 1/1).

In some aspects, an elemental metal composition may have a field effect on biological tissue (e.g., it may alter an electrostatic and/or electromagnetic field of a biological tissue). The field effect may be used to impact one or more biological processes. As used herein, a biological process may be impacted if it is altered in any manner. For example, a process may be enhanced (e.g., the amplitude, degree, and/or speed of the process may be increased). In other embodiments, a process may be suppressed (e.g., the amplitude, degree, and/or speed of the process may be reduced). In further embodiments, a process may be established, redirected, or terminated.

In one aspect, compositions of the invention may be used therapeutically to treat certain conditions in animals (e.g., humans, pets, agricultural animals, etc.). Conditions that can be treated include skin diseases, pain, injuries, and other conditions described herein.

In another aspect, compositions of the invention may be used in agriculture and/or horticulture to alter certain aspects of plant physiology. In certain embodiments, plant growth, seed germination, fruit and/or vegetable ripening, and/or other aspects of plant physiology may be modified as described herein (e.g., to preserve fruits or vegetables, to increase seed germination, etc.).

Elemental metal compositions of the invention may be prepared and/or packaged in different formulations and/or configurations depending on their intended use as described herein.

The following description provides details and examples of different elemental metals, coatings, and devices of the invention along with useful applications for animals and plants. It should be appreciated that different applications of the invention may involve different elemental metals, coatings, and/or containers. In addition, it should be appreciated that a predetermined electrostatic and/or electromagnetic field effect may not be the only factor that influences or determines the type of metal, coating, and/or container that is used for a particular application. For example, properties such as toxicity, availability, cost, ease of use, and other properties described herein, or any combination thereof may inform the choice of appropriate metal(s), coating(s), and/or container(s).

Elemental Metals:

Aspects of the invention relate to compositions and devices comprising certain configurations of one or more elemental metals and methods for their use. Applicant has discovered that certain configurations of elemental metals may have therapeutic and/or biological effect(s) when contacted to a biological tissue surface. In one embodiment, and without wishing to be bound by theory, therapeutic and/or biological effect(s) are related to a capacitor and/or field effect of the elemental metal composition and not to specific chemical interactions between the elemental metal(s) and one or more biological molecules within a biological tissue.

As used herein, an elemental metal may be a transition metal, a metalloid, or other metal that can be stable as a free metal in nature. A transition metal may be scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, ununnilium, unununium, or ununbium. Transition metals have valence electrons in more than one shell, and can exist in different oxidation states. Transition metals include metals that can produce a magnetic field (iron, cobalt, and nickel). A metalloid may be boron, silicon, germanium, arsenic, antimony, tellurium, or polonium. Some metalloids are semi-conductors (silicon and germanium). Other metals that can exist as free metals include aluminum, gallium, indium, tin, thallium, lead, and bismuth. These metals only have valence electrons in their outer shell and do not exist in more than one oxidation state.

In contrast, alkali metals and alkaline earth metals are not present as free metals in nature and are not elemental metals as used herein. Alkali metals include lithium, sodium, potassium, rubidium, cesium, and francium. Alkali metals are reactive metals with one electron in their outer shell and they readily lose this electron in an ionic bond with other elements. Alkaline earth metals include beryllium, magnesium, calcium, strontium, barium, and radium. Alkaline earth metals are also very reactive metals and are not stable as free metals in nature.

According to the invention, any elemental metal or combination of elemental metals may be included in a biologically effective composition if it imparts suitable capacitor and/or field effect(s) to the composition (e.g., when coated with one or more non-metallic materials). However, it should be appreciated that certain biochemical properties may be considered and evaluated when choosing an elemental metal, even though the biological effectiveness of the composition does not depend on specific chemical interactions between the elemental metal and one or more biological molecules. For example, a composition preferably is not harmful (e.g., non-toxic), particularly if it is not contained within a physical device that protects an animal, plant, or the environment from exposure to the composition. According to one aspect of the invention one or more non-harmful metals may be chosen. In another aspect, metals with different electrochemical properties may be combined to produce a composition with an appropriate capacitor and/or field effect when contacted with biological tissue. In yet another aspect, an elemental metal composition may include only (or primarily) elemental metal(s) that are naturally present in a biological tissue (animal or plant) that is being treated. For example, a composition for use with a human may include one or more of iron, copper, magnesium, and selenium. In one embodiment, the relative amounts of two or more elemental metals in a composition may be similar (e.g., the same or about the same) as their relative amounts in a biological tissue. However, in other aspects any one or more elemental metals may be included in a composition of the invention. In one embodiment, any two or more different elemental metals (e.g., 2, 3, 4, 5, 6, 7, 8, 9, 10, 10-15, 15-20, or more) may be combined. Two or more elemental metals may be included as a mixture or as an alloy. A composition may contain a combination of one or more elemental metal(s), and one or more alloys. Alternatively, a composition may contain only elemental metal(s) or only alloy(s). Ratios of different metals (e.g., in mixtures or in alloys) in different compositions of the invention may range from 1:1000 to 1000:1. However, higher, lower, or intermediate ratios may be used (e.g., 100:1, 50:1, 10:1, 5:1, 1:1, 1:5, 1:10, 1:50, 1:100, etc.). It should be appreciated that any combination of two or more (e.g., 3, 4, 5, 6, 7, 8, 9, 10, etc.) different elemental metals may be used. For example, a composition may include iron, zinc, copper, aluminum, silicon, or any combination of two or more thereof (e.g., all thereof). In some embodiments, a composition may include iron and zinc. In some embodiments, a composition may include iron and copper. In some embodiments, a composition may include, zinc and copper. Any one of these compositions also may include aluminum, silicon, or a combination or aluminum or silicon. In some embodiments, the ratio of iron to zinc may be between about 10/1 and about 1/1 (e.g., 10/1, 5/1, 2/1, 1/1) or any higher, lower, or intermediate ratio. In some embodiments, the ratio of zinc to copper may be between about 10/1 and about 1/1 (e.g., 10/1, 5/1, 2/1, 1/1) or any higher, lower, or intermediate ratio. In some embodiments, the ratio of copper to aluminum may be between about 10/1 and about 1/1 (e.g., 10/1, 5/1, 2/1, 1/1) or any higher, lower, or intermediate ratio. In some embodiments, the ratio of aluminum to silicon may be between about 10/1 and about 1/1 (e.g., 10/1, 5/1, 2/1, 1/1) or any higher, lower, or intermediate ratio. Any specific combination of the above ratios may be used in a composition of the invention. For example, iron, zinc, copper, aluminum, and silicon may be present in any ratio of the five elements relative to each other (for example, in relative order of iron/zinc/copper/aluminum/silicon from about 10,000/1,000/100/10/1 to about 1/1/1/1/1, e.g., about 16/8/4/2/1, about 20/4/2/2/1, about 8/4/2/2/1, about 50/10/2/1/1, about 50/50/25/25/1, about 50/25/5/5/1, or any other combination of ratios described herein).

In certain aspects, a composition may include oxidized or reduced forms of elemental metal(s). However, in some embodiments, oxidized and/or reduced forms should not represent more than 50%, for example, not more than 25%, not more than 20%, not more than 15%, not more than 10%, not more than 5%, not more than 1%, not more than 0.1%, or not more than 0.01% of the weight or volume of the elemental metal in the composition.

In certain aspects of the invention, a composition may include metals that are non-elemental in addition to one or more elemental metals. However, in some embodiments the non-elemental metal(s) do not constitute more than 50%, for example not more that 40%, 30%, 25%, 20%, 15%, 10%, 5%, 1%, or 0.1% of the weight or volume of metal in the composition. Accordingly, the elemental metal(s) may represent more than 50%, for example more than 60%, 70%, 75%, 80%, 85%, 90%, 95%, 99%, or 99.9% of the weight or volume of metal in the composition. However, the total elemental metal(s) may represent from more than 99% to less than 1% of the total weight or volume of a composition (e.g., about 90%, 75%, 50%, 25%, 20%, 15%, 10%, 5%, 1%, or more or less).

Accordingly, in some embodiments, a composition or device of the invention includes only or at least 50%, 60%, 70%, 80%. 90%, 95%, 99%, or more non-ionic metal. In some embodiments, an elemental metal is provided in an inert or non-reactive matrix or coating (e.g., carbonaceous) to prevent the production of ionic metals (e.g., borates, sulfates, etc.).

Particulate Forms

In one aspect, a composition of the invention includes one or more elemental metals in particulate form. Accordingly, in some embodiments, an elemental metal is provided in an insoluble form within a matrix. The diameter of a metal particle may range from several mms (e.g., 1 cm) to several nms. However, in certain embodiments bigger or smaller particles may be used. Accordingly, a metal particle may be about 1 mm in diameter, about 100 microns in diameter, about 10 microns in diameter, about 1 micron in diameter, about 100 nms in diameter, about 10 nms in diameter, about 1 nm in diameter. A composition may contain from one to dozens, hundreds, thousands, millions, billions or more particles per unit volume. The sizes of the particles in a preparation may be uniform (e.g., all having approximately the same diameter) or may be distributed across a range of diameters (e.g., a narrow range with for example 90% of the particles within a two to ten fold range of diameter size, or a broader range with for example 90% of the particles within a 100 to 1,000 fold range of diameter size). Accordingly, compositions of the invention may include metal balls, metal filings, metal powders, nanoparticles (e.g., particles between 0.1 to 10 nm in diameter). In one embodiment, particles have a diameter that is less than about 100 microns, for example less than about 50 microns, or less than about 10 microns. For example, particles with a diameter of about 40 microns or less may be selected using a 325 mesh sieve which excludes particles with a diameter greater than about 40 microns. It should be appreciated that the shape of the metal particles is not necessarily spherical. A metal particle may be a sphere or approximated to a sphere in some embodiments. However, in other embodiments, a particle may be ovoid, elongated, rectangular, irregular, etc. It should be understood that the reference to a diameter in the context of a particle relates to an average dimension across the particle. In the context of a sphere, a diameter is the diameter of the sphere. In the context of a less-spherical, or non-spherical particle, a diameter refers to an average dimension of the particle (e.g., an average of the longest distance, an average of the shortest distance, or an average of all distances, between two sides of the particle).

Particles of different sizes may be obtained or prepared using any suitable method. In one embodiment, particle sizes may be selected by sieving elemental metal particles using different meshes (e.g., 200 mesh, 300 mesh, 325 mesh, etc.).

These and other aspects of different elemental metals that can be used according to the invention are described in more detail below.

Matrix Materials (e.g., Coatings):

In one aspect of the invention, compositions and/or devices contain at least one elemental metal coated with a layer of non-metallic material (e.g., a layer of one or more non-conducting or semi-conducting materials). In another aspect of the invention, compositions and/or devices contain at least one elemental metal mixed with a preparation of non-metallic material (e.g., particles of one or more non-conducting or semi-conducting materials). According to the invention, a matrix (e.g., a coating) that separates at least a fraction (e.g., 100% or less, for example, about 80%, 70%, 60%, 50%, 40%, 30%, 20%, 10%, 5%, or less) of the elemental metal particles from each other may enhance one or more electrostatic and/or electromagnetic properties of the invention by increasing the capacitance of an elemental metal preparation.

Coatings may be organic material(s) (e.g., organic waxes, etc.), synthetic material(s), or any combination thereof. Examples of suitable coating materials include VASELINE® (Conopco, Inc. d/b/a Unilever), petroleum jellies, oils, beeswax, lanolin, etc.). It should be appreciated that certain materials may be used i) as coating materials to impart suitable electrical properties (e.g., conductance, field-effect, capacitance, etc.) on an elemental composition and/or ii) as mixture components to impart suitable physical properties (e.g., viscosity, malleability, etc.) on an elemental composition. For example, lanolin may be used as a coating and/or as an emulsifier. In some embodiments, a material (e.g., lanolin) may be used primarily for its physical effect on a composition (e.g., an emulsifier). In some embodiments, an oil (e.g., a mineral, animal, and/or a vegetable oil) may be used to modify one or more physical properties (e.g., to increase stickiness). In some embodiments, an animal fat may be used as the matrix or may be added to a different matrix to modify one or more physical properties. In some embodiments, one or more other materials or compounds may be used to increase or decrease the malleability, flexibility, and/or stickiness of a composition. However, their effect on the electrical properties of the composition also should be considered (e.g., evaluated experimentally).

In one aspect, a preparation of elemental metal particles may be mixed with particles of a non-conducting or semi-conducting material (e.g., glass, silicone, wool, cotton, etc.). Any suitable ratio may be used. In one embodiment, the size range of the particles of elemental metal may be the same as that of the non-conducting or semi-conducting material. In one embodiment, the size range of the particles of elemental metal may be different from that of the non-conducting or semi-conducting material.

In one aspect, a composition may be viscous or semi-solid (e.g., waxy) at room temperature (or other temperature that is characteristic of the environment of use) so that it is easy to apply to a surface (e.g., skin). However, in certain embodiments, a composition may be liquid at room temperature (or other temperature that is characteristic of the environment of use). In yet other embodiments, a composition may be solid or grainy at room temperature (or other temperature that is characteristic of the environment of use). Liquid solutions may be particularly useful for applying to surfaces where physical spreading of a cream/ointment is not practical (e.g., for spreading/spraying over relatively large areas (e.g., agricultural areas). However, solid compositions also may be used in situations where a large number of units or volumes of an elemental metal composition may be dispersed over a large area (e.g., an agricultural area). Any form of composition may be contained within an enclosure (e.g., a container such as a solid container, a pouch, a sac, etc.). In embodiments, a composition of the invention may be provided as an aerosol or other form that can be readily dispersed over an area of interest (e.g., a spray that can be sprayed onto a patient skin or a spray that can be sprayed over plants in a greenhouse or on a field).

In one aspect, a coating is sufficiently malleable to be mixed with an elemental metal so that the coating covers at least a portion of the elemental metal surface thereby forming an interface between the elemental metal(s) and the coating material(s). In one embodiment, the coating may cover between 1% and 100%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% of the surface of the elemental metal (e.g., when inspected visually). FIG. 1 illustrates an example of several metal particles that are covered with a coating material.

In one embodiment, an elemental metal may be covered with a coating material under conditions that are suitable for preparing a mixture with the coating material covering the elemental material or a portion thereof (e.g., a wax may be mixed with elemental metal at a temperature sufficiently high to melt the wax). The resulting preparation subsequently may be used under different conditions (e.g., at a lower temperature).

As with the elemental metals, different properties may be considered when selecting an appropriate coating material. Properties may include conductivity, toxicity, availability, malleability, stability, etc., or any combination of two or more thereof.

It should be appreciated that similar elements and considerations may be used when preparing a composition with a particulate matrix (or a matrix that contains both particulate material and non-particulate coating material). In addition, the average size of matrix particles may be similar or different from the average size of the elemental metal particles in a composition. Furthermore, different ratios of elemental metal particles to matrix particles may be used (e.g., about 1000:1; 100:1; 10:1; 1:1; 1:10; 1:100; 1:1000; or higher, lower, or intermediate ratios).

Accordingly, in different aspects of the invention, matrix materials may be solid, liquid, particulate, non-particulate, or a combination of two or more thereof.

Properties of Elemental Metals and Matrix Materials (e.g., Coating Materials):

Aspects of the invention may use different materials (e.g., elemental metals and/or matrix materials) based on certain properties such as toxicity, availability, cost, etc. The following paragraphs describe different properties of materials including elemental metals and provide groupings of elemental metals and other materials based on properties that may be useful for certain applications. It should be understood that different properties described herein for individual metals may be considered for compositions including only one elemental metal, a mixture of two or more elemental metals, an alloy of two or more metals, or any combination of two or more thereof. However, certain metals may be less toxic when in combination with other elements. For example, certain metals may be less toxic or hazardous when in an alloy than when present as a pure metal.

In one aspect, safety and health considerations may be considered when selecting or using a material or element. In one embodiment, compositions may include only non-hazardous and/or non-radioactive metals (i.e., no hazardous and/or radioactive metals). In one embodiment, compositions may include only non-hazardous and/or non-radioactive alloys (e.g., alloys that contain no metals that are inherently hazardous and/or radioactive).

The hazardous properties of a metal may be rated according to HMIS (Hazardous Materials Information System). In one embodiment, non-hazardous metals are those with a health rating of 2 or lower (ratings typically range from 0-4).

In one embodiment, a composition of the invention does not contain any of the following radioactive elements: technetium, bismuth, (metalloids) polonium and astatine, actinium, thorium, protactinium, uranium, neptunium, plutonium, americium, curium, berkelium, californium, einsteinium, fermium, mendelevium, nobelium, lawrencium, rutherfordium, dubnium, seaborgnium, bohrium, hassium, meitnerium, darmstadtium, unununium, ununbium, ununtrium, ununquadium, ununpentium, ununhexium and radioactive elements that are higher on the periodic table. However, one or more such elements may be used in certain embodiments, for example by providing them in a shielding container or device that reduces the amount of damage that may be caused by radiation. Also, certain radioactive metals emit a low energy radiation and may be used without a shielding container or device. For example, indium is only slightly radioactive (beta decay), is not harmful, and may be useful in compositions and methods of the invention. Similarly, other slightly radioactive metals may be used.

In one embodiment, a composition of the invention does not contain a spontaneous combustible or explosive solid element or an element with any other dangerous physical property. For example, individual metals with Hazardous Material Information System (HMIS) ratings of 3 or greater in flammability and other health properties may be excluded from compositions of the invention (except in the form of an alloy or mixture that is not as physically dangerous). Examples of metals and alloys that may be physically dangerous include, Lanthanum, Manganese, Hafnium (10 micron particles spontaneously ignite), Osmium, and Phosphorus.

Similarly, in certain embodiments metals that are generally (grossly) toxic may be excluded from compositions of the invention. Examples of metals that may be toxic to animal or plant life include (especially at high concentrations) Hafnium, Tungsten, Manganese, Chromium, Osmium, Cobalt, Thallium, Phosphorus, Mercury, Arsenic, and Lead. However, in one embodiment, any of these metals may be non-toxic or less toxic when used as a stable alloy (e.g., a manganese, chromium, or phosphorous alloy). Also, certain of these metals (e.g., manganese and cobalt) may be important metals for the growth of some organisms (e.g., plants) and therefore non-toxic when used in suitable amounts (e.g., relatively low concentrations).

Other toxic metals include those with multiple toxicities as determined by Occupational Safety and Health Administration (OSHA) and Department of Environmental Protection (DEP), for example Cadmium, Hafnium, Antimony, Mercury, Arsenic, Lead, Osmium, and Cobalt. In other embodiments, metals that are toxic when inhaled may be excluded (e.g., Hafnium, Tungsten, Manganese, Osmium, Cobalt, Cadmium, Thallium, Phosphorus, Antimony, Arsenic, and Lead). In other embodiments, metals that are toxic when ingested orally may be excluded (e.g., Cobalt, Cadmium, Thallium, Phosphorus, Antimony, Arsenic, and Lead). In further embodiments, metals that are toxic when absorbed through the skin, and/or metals that are skin irritants, and/or metals that cause ulcerations may be excluded. Examples of such metals include Hafnium, Manganese, Osmium, Cobalt, Thallium, Phosphorus, and Arsenic. In yet further embodiments, CNS toxic elements or alloys that contain these elements may be excluded (e.g., Tungsten, Manganese (Parkinson's), Lead, Antimony, and Mercury). In other embodiments, toxic metals and/or alloys that destroy mucosal membranes and/or skin may be excluded (e.g., Chromium, Osmium, Thallium, and Phosphorus). In certain embodiments, metals that are toxic to plants may be excluded (e.g., Aluminum at high concentrations). In other embodiments, carcinogen metals (e.g., as defined by Occupational Safety and Health Administration, Food and Drug Administration, or other organizations) may be excluded (e.g., Zirconium, Chromium, Tungsten, Cobalt, Nickel, Cadmium, Thallium, and Alloy of Chromium-Nickel-Cobalt). However, it should be appreciated that any one of more of these elements may be used if provided in a suitable container or protective device that reduces any undesirable properties of the metals to an acceptable level in view of the anticipated exposure to animal (e.g., human) and/or plant.

According to aspects of the invention, nuisance metals may be excluded. However, in many embodiments nuisance metals may be used if the nuisance factor does not outweigh the anticipated or observed physiological benefit. Nuisance metals may have an HMIS rating of 2 on health exposure. Non-limiting examples of nuisance metals include: Scandium (Flammability 2-powder, Health 1-inhalation, Reactivity 0); Yttrium (Flammability 3-powder spontaneous ignition, Health-1, Reactivity 0); Titanium (Flammability 3-powder, Health 1-inhalation, Reactivity 1); Vanadium (Flammability 0, Health 2-chronic inhalation, Reactivity 0)-is used in medical devices; Niobium (Flammability 0, Health 0, Reactivity 0); Tantalum (Flammability 0, Health 1-inhalation, Reactivity 0); Molybdenum (Flammability 0, Health 0, Reactivity 0); Rhenium (Flammability 0, Health 0, Reactivity 0); Iron (Flammability 0, Health-ingestion 2, Reactivity 0); Ruthenium (Flammability 1, Health 1, Reactivity 0); Rhodium (Flammability 1, Health 1, Reactivity 0); Iridium (Flammability 1, Health 0, Reactivity 0); Nickel (low overall toxicity except on ingestion and then carcinogenic and reactivity is low); Palladium (Flammability 0, Health 1-inhalation, Reactivity 0); Platinum (Flammability 0, Health 1, Reactivity 0); Copper (Flammability 2-dust, Health 1, Reactivity 1); Silver (Flammability 2-powder, Health 1-skin absorption-Argyrosis, Reactivity 1); Gold (Flammability 1-powder, Health 1-ingestion, Reactivity 0); Zinc (Flammability 1-powder, Health 1-fume ingestion, Reactivity 0); Aluminum (Flammability 1-powder, Health-ingestion, Reactivity 2-exothermic with iron and water); Gallium (Flammability 0, Health 1-ingestion, Reactivity 0); Indium (Flammability 0, Health 1-ingestion, Reactivity 0); and Tin (Flammability 3-powder, Health 2-inhalation, Reactivity 0).

Non-limiting examples of nuisance metalloids include: Boron (Flammability 3-powder spontaneous ignition, Health 2-toxic fumes if burning & ingestion, Reactivity 0); Silicon (Flammability 0, Health 1-inhalation, Reactivity 0); Germanium (Flammability 0, Health 0, Reactivity 0); and Tellurium (Flammability 0, Health 3-ingestion, inhalant, Reactivity 0). It should be appreciated that nuisance metalloids may be used in certain embodiments if appropriate protective measures are taken.

Non-limiting 1xamples of nuisance non-metals that may be used as a matrix (e.g., a coating) include Carbon (Flammability 1-powder Health 0, Reactivity 0); Sulfur (Flammability 1-powder, Health 1-ingestion, Reactivity 0); and Selenium (Flammability 1-powder, Health 1-inhalation, Reactivity 1).

In some aspects of the invention, compositions may exclude materials (e.g., metals) that cause acute inflammation or that are readily absorbed through the skin of an animal (e.g., a human). However, such metals may be used if they are used in low amounts or if they are provided in a container or suitable device that protects the skin from direct contact with the metal. Non-limiting examples of such metals include: Ruthenium (strongly stains skin); Nickel and Silver (Argyrosis).

According to aspects of the invention, useful elements (e.g., elemental metals and alloys) that are readily available in particulate form and at a reasonable cost include: Yttrium, Titanium, Vanadium, Molybdenum, Iron, Nickel, Palladium, Copper, Silver, Zinc, Boron, Aluminum, Gallium, Indium (shot), Carbon, Silicon, Germanium, Tin, Sulfur, Selenium, and Tellurium. Other useful metals that may be more expensive include: Scandium, Niobium, Tantalum, Rhenium, Ruthenium, Rhodium, Iridium, Platinum, and Gold.

According to aspects of the invention, the following useful elements and alloys may cause some/minor skin irritation (HMIS 0 or 1) in finely divided form: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Boron, Aluminum, Gallium, Indium, Silicon, Germanium, Tin, Sulfur, Selenium, and Tellurium.

Elements that may be readily available in particulate or finely divided powder or nanoparticle forms include: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Boron, Aluminum, Indium, Carbon, Silicon, Germanium, Tin, Sulfur, Selenium, and Tellurium (note that Gallium may be available as soft/liquid).

According to aspects of the invention, the following elements should be used with care to prevent ingestion by an animal (e.g., a human) or leaching into the environment: Yttrium, Scandium, Titanium, Vanadium, Tantalum, Molybdenum, Rhenium, Iron, Ruthenium, Rhodium, Iridium, Nickel, Palladium, Platinum, Copper, Silver, Gold, Zinc, Boron, Aluminum, Gallium, Indium, Carbon, Silicon, Germanium, Tin, Sulfur, Selenium, and Tellurium. Certain of these elements may be non-toxic or even beneficial in low amounts but toxic in higher amounts (e.g., vanadium which is an essential element required in low amounts for some biological tissue or organisms including lower invertebrates, but often toxic in higher amounts). Niobium also should be used with care as it may cross the placental barrier in animals.

In other aspects of the invention, the following elements may be particularly useful for agricultural applications: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Boron, Aluminum, Gallium, Indium, Carbon, Silicon, Germanium, Tin, Sulfur, Selenium, and Tellurium. For example, sodium, potassium, calcium, magnesium, phosphorus, and sulfur may be essential macronutrients for certain plants. Chorine, iron, boron, manganese, zinc, copper, molybdenum, and nickel may be essential micronutrients for certain plants. In addition, silicon, sodium, cobalt, and selenium may be beneficial elements for certain plants.

Although less expensive and readily available elements (e.g., metals) may be selected, it should be appreciated that any of the metals described herein may be used in aspects of the invention. Examples of elements that may be readily obtained and that are relatively inexpensive in finely divided form include: Titanium, Vanadium, Molybdenum, Iron, Nickel, Palladium, Copper, Silver, Zinc, Boron, Aluminum, Indium, Carbon, Silicon, Germanium, Tin, Sulfur, Selenium, and Tellurium. Examples of other elements that may be used but that are more difficult to obtain and/or more expensive include: Yttrium, Scandium, Niobium, Tantalum, Rhenium, Ruthenium, Rhodium, Iridium, Platinum, Gold, and Gallium (soft).

In some aspects of the invention, elements and alloys that have FDA approval may be selected for certain human applications. Examples include: Titanium (approved for implants and coatings); Vanadium (approved for implants and coatings); Tantalum (approved for implants, dental and surgical instruments); Molybdenum (approved for prosthetic devices, trace element in plants and animals); Iron (essential element, approved for supplements, and has multiple approvals); Iridium (approved for surgical tools); Palladium (approved for multiple uses in alloys); Platinum (approved for multiple uses); Copper (approved for multiple uses); Silver (approved for multiple uses); Gold (approved for multiple uses); Zinc (approved for multiple uses); Carbon (approved for multiple applications); Silicon (approved for multiple uses); Germanium (alloy, approved for uses); Tin (approved for multiple uses); Sulfur (approved for multiple uses); and Selenium (approved for multiple uses). It should be appreciated that compositions of the invention may be used for these and/or other uses. However, the fact that a compound has been approved for one use suggests that it may be suitable (e.g., non-toxic, non-irritant, etc.) for other uses.

It should be appreciated that certain metals that are individually toxic may have reduced toxicity when in the form of an alloy or mixture. Relative toxicities may be determined by one of skill in the art and appropriate alloys may be selected based on their toxicity profiles.

In one aspect, one or more alloys listed with American Iron and Steel Institute (AISA) may be used, for example, Iron Alloys with: Aluminum, Silicon, Manganese, Chromium, Vanadium, Molybdenum, Niobium (columbium), Selenium, Titanium, Phosphorus, Cobalt, Tungsten, Boron, Iron-Carbon Alloys with: Silicon, Phosphorus, Sulfur, Manganese, Nickel, Chromium, Molybdenum, Copper, and/or Titanium.

In one aspect, prosthetic alloys may be used. For example, strongly adherent and passivating surface oxides, such as titanium oxide (TiO2) on titanium-based alloys and chromium oxide (Cr2O3) on cobalt-based alloys may be used.

In one aspect, ferrous, cobalt-based, or titanium-based alloys may be used: for example, cold-worked stainless steel; cast Vitallium; a wrought alloy of cobalt, nickel, chromium, molybdenum, and titanium; titanium alloyed with Aluminum and vanadium; and commercial-purity titanium may be used.

In one aspect, certain alloys may be modified by nitriding or ion-implantation of surface layers of enhanced surface properties. For example, one or more of the following alloys may be used: as cast Co—Cr—Mo alloy; Bronze: copper and tin plus traces of other elements; Brass: copper and zinc; Bearing alloys: Babbitt metal, tin (Sn), antimony (Sb) and copper (Cu), copper, or silver (Ag); Corrosion-resisting alloys: Stainless steels: Austenitic, Ferritic and Martensitic formulas; Aluminum alloys: Al-lithium, chromium (Cr), nickel (Ni), Monel, an alloy of nickel and copper; Inconel: which contains chromium and iron (Fe), Spiegeleisen: iron-manganese-carbon-silicon; Dental alloys: Amalgams silver and mercury (Hg), tin, copper, and zinc (Zn), Gold-base (Au), silver, and copper, palladium and platinum; Vitallium an alloy of cobalt, chromium, molybdenum, and nickel; Die-casting alloys: Zinc-base: aluminum and copper; Aluminum-base: Silicon, copper, iron, silicon; Eutectic alloys: copper with silver, tantalum carbide (TaC) fibers in a matrix of a cobalt-rich alloy; Fusible alloys: lead, cadmium, bismuth, tin, antimony, and indium, bismuth; and/or, Inter metallics: Mu-metal (nickel-iron-copper-molybdenum).

In one aspect, high-temperature alloys may be used, including one or more of: Stainless steels: Cr, Ni, and molybdenum; both nickel-base and cobalt-base alloys, Nichrome, a nickel-base alloy containing, chromium and iron; René-41 contains, chromium, aluminum, titanium (Ti), cobalt (Co), molybdenum, iron, carbon (C), boron (B), and nickel; and/or Molybdenum-base alloys.

In one aspect, joining alloys may be used. For example, one or more of the following may be used: copper-zinc, tin brass, silicon-aluminum eutectic alloy, aluminum-containing magnesium, and/or lead-tin alloys.

In one aspect, light-metal alloys may be used. For example, one or more of the following may be used: Aluminum and magnesium (Mg), aluminum and copper, and magnesium and aluminum; ternary (three-element) and/or more complex: aluminum-zinc-magnesium systems.

In other aspects, any one or more of the following alloys may be used: low-expansion alloys (e.g., Invar (iron-nickel), Kovar (5 iron-nickel-cobalt), etc.); magnetic alloys (e.g., silicon-ferrite); permalloy (nickel-iron) and some comparable cobalt-base alloys; ceramic ferrites; Inicos, Alnico-4 (iron-nickel-aluminum-cobalt), RCo5, where R is samarium (Sm), lanthanum (La), cerium (Ce); precious-metal alloys (e.g., yellow gold which is an Au—Ag—Cu alloy, white gold which is Au-nickel, silver, or zinc, which change the color from yellow to white); the alloy platinum (Pt)-rhodium (Rh)-platinum; sterling silver; shape memory alloys; gold alloyed with cadmium; nickel and titanium known as nitinal; thermocouple alloys; Chromel: nickel and chromium; Alumel: nickel, aluminum, chromium, and silicon; the widely used Chromel-Alumel thermocouple; superconducting alloys (e.g., niobium and titanium, niobium and tin, vanadium and gallium, niobium and germanium, niobium and aluminum, etc.); lead-indium; lead-gold (PbAu); ceramic; copper oxide-based materials; yttrium-barium-copper-oxygen; bismuth-strontium-calcium-copper-oxygen; thallium-barium-calcium-copper-oxygen; etc.; or any combination of two or more of the above.

Electrostatic and/or Electromagnetic Field Effects

The electrochemical properties of a composition of the invention may be determined based on the elemental metals that are used. It is expected that a wide range of electrochemical properties may be beneficial. However, one of ordinary skill can test different ratios and content for their effect on different biological systems. Accordingly, one of ordinary skill can optimize a composition of the invention for a particular use.

The following non-limiting properties may be considered when determining which metals or mixtures of metals to use: electroresistivity, electron-nucleus "charging characteristics," reduction or oxidation potential, electrostatic properties, electro-negative characteristics, electro-positive characteristics. These and other features are described in more detail in the following paragraphs.

In one aspect, elements that due to their particular electroresistivity (micro ohm-cm @ normal conditions) may be useful in elemental metal compositions of the invention include elements with high or low electroresistivity. Different electroresistivity properties may be used depending on the biological application and the desired biological effect (e.g., the desired intensity of the biological effect). Suitable electroresistivity also may be influenced by other metals in the composition and by the coating material(s) and the configuration of the final compositions (e.g., an ointment or cream, or enclosed within a container, etc.). Accordingly, in some embodiments an elemental metal composition may include one or more of a low resistivity, semi-conductor, or high resistivity (electron deficient and/or non metal) metal(s).

In one aspect, low resistivity metals include: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Aluminum, Gallium, Indium, Silicon, and/or tin.

In one aspect, semi-conductors (Metalloids) include: Boron, Silicon, Germanium, and/or Tellurium.

In one aspect, High resistivity elements include: Boron (electron deficient), Carbon, Germanium, Silicon, Sulfur, Selenium, and/or Tellurium.

In one aspect, elements that due to their electron-nucleus "charging characteristics" in the form of electronegativity (Pauling) may be useful in elemental metal compositions of the invention include those that are not so high as to be dangerously reactive. However, it should be appreciated that combinations of high and low electronegativity may yield compositions with a high "capacitance." Different electronegativity properties may be used depending on the biological application and the desired biological effect (e.g., the desired intensity of the biological effect). Suitable electronegativity also may be influenced by other metals in the composition and by the coating material(s) and the configuration of the final compositions (e.g., an ointment or cream, or enclosed within a container, etc.).

In one embodiment, compositions contain one or more metals with electronegativity values between 1.2 and 2.56 Paulings. For example, Molybdenum (1.16), Scandium (1.3), Yttrium (1.3), Aluminum (1.5), Titanium (1.5), Tantalum (1.5), Vanadium (1.6), Niobium (1.6), Zinc (1.6), Gallium (1.6), Indium (1.7), Silicon (1.8), Iron (1.8), Nickel (1.8), Tin (1.8), Copper (1.9), Silver (1.9), Rhenium (1.9), Germanium (2.01), Boron (2.04), Tellurium (2.1), Rhodium (2.2), Platinum (2.2), Palladium (2.2), Ruthenium (2.2), Iridium (2.2), Gold (2.4) Sulfur (2.5), Carbon (2.55), and/or Selenium (2.55).

In one aspect, elements that due to their relatively low, medium or high oxidation potential may be particularly useful in elemental metal compositions of the invention may nonetheless have special handling considerations as discussed herein.

In one aspect, low oxidation potential metals include: Gallium, Indium, Silicon, Nickel, Tin, Copper, Silver, Ruthenium, Germanium, Boron, Tellurium Rhodium, Iridium (mildly basic), Palladium, Platinum, Gold, Carbon, and/or Selenium.

In one aspect, moderate oxidation potential metals (e.g., metals with some instability when exposed to flame, air, oxygen, or water) include: Aluminum, Zinc, Iron, Titanium, Niobium (5 micron spontaneous ignition in air), Tantalum, and/or Rhenium.

In one aspect, elements with combined extremes in reduction-oxidation potential (in solution versus hydrogen electrode) may be particularly useful in certain combinations.

In one aspect, elements with high electro-positive potential (reactive chemically) include: Yttrium, Scandium, Titanium, Vanadium, Ruthenium, Nickel, Niobium, Zinc, Iron, Aluminum, Gallium, Indium, Tin, Sulfur, Selenium, and/or Tellurium. In one embodiment, elements with high electro-negative potential (least reactive chemically) include: Copper, Silver, Gold, Rhodium, Platinum, and/or Palladium.

In one aspect, elements with a moderate degree of negative reduction potential (between about 1.8 and 2.0 Paulings) may be useful in some elemental metal compositions of the invention for human use. For example, Zinc, Gallium, Indium, Silicon, Iron, Nickel, Tin, Copper, and/or Silver may be used.

In one embodiment, these elements form particularly effective energy compounds when mixed with elements from the extremes of the electro-motive series. For example, one or more elements with a moderate degree of negative reduction potential may be mixed with one or more elements below 1.6 Pauling such as Molybdenum (1.16), Scandium (1.3), Yttrium (1.3), Aluminum (1.5), Titanium (1.5), Tantalum (1.5), Vanadium (1.6), and/or Niobium (1.6). In another example, one or more elements with a moderate degree of negative reduction potential may be mixed with one or more elements above 1.9 Pauling such as Rhenium (1.9), Germanium (2.01), Boron (2.04), Tellurium (2.1), Rhodium (2.2), Platinum (2.2), Palladium (2.2), Ruthenium (2.2), Iridium (2.2), Gold (2.4) Sulfur (2.5), Carbon (2.55), and/or Selenium (2.55).

In one aspect, elements with particular electrostatic properties may be useful in elemental metal compositions of the invention. For example, tantalum may be useful, because it has the most capacitance per volume of any substance. Ruthenium may be useful, because it has multi-valence states and high capacitance. Boron may be useful in some embodiments, because it has poor thermal and electrical conductivity. Gallium may be useful in some embodiments, because it is a "poor metal" and soft/liquid. Indium may be useful in some embodiments, because it has a unique response to electric fields. Carbon may be useful in some embodiments as a coating or other matrix. Carbon also may be used in one or more alloys (e.g., carbon steels), because it has multiple forms with variable electrostatic properties. Silicon may be useful in some embodiments, because it is a stable semi-conductor. Germanium may be useful in some embodiments, because it is a semi-conductor and has a unique response to infra-red radiation. Sulfur may be useful in some embodiments, because it has multiple crystalline morphologies. Selenium may be useful in some embodiments, because of its rectifier functions and it is radiant to electrical energy. Tellurium may be useful in some embodiments, because it is slightly photosensitive.

In one aspect, "poor metals" or "post transition metals" may be used (metals occurring between metalloids and transition metals that are more electropositive than many transition metals). For example, Aluminum, Gallium, Indium, and/or Tin may be used.

In one aspect, certain elements and/or alloys may be particularly useful in elemental metal compositions of the invention. For example, metals with a non-chemical bonding and/ or an inducible and/or fluctuating electrostatic "field effect" may be particularly useful. In one embodiment, Yttrium, Scandium, Molybdenum, Palladium, Silver, Zinc, Aluminum ("elemental clustering"), Iron, Copper, Gallium, Indium, Carbon, Silicon, Germanium, Sulfur, Selenium, and/or Tellurium may be particularly useful.

In one aspect, elements and alloys that have ferromagnetic potential (ferro-magnetic group) may be non-toxic and useful for compositions of the invention. For example, Iron, Cobalt Nickel, Platinum, and/or Yttrium (slight magnetic susceptibility) may be used.

In one aspect, metals in the Platinum metal group may be useful, for example, Platinum, Palladium, Ruthenium, Rhodium, and/or Iridium. In one embodiment, Osmium is not used.

Methods for Preparing Capacitor Compositions Comprising Coated Elemental Metals

According to the invention, certain metal powders may be thermally unstable in the presence of oxygen, because the powders possess a high surface area per unit mass. Very fine metal powders can burn in air (pyrophoricity) and are potentially explosive. Therefore clean handling of powder may be important. Suitable methods for handling powders may include venting, controlled oxidation to passivate particle surfaces, surface coating, minimization of sparks or heat sources, etc., or any combination thereof. Some respirable fine powders pose a health concern and can cause disease or lung dysfunction: the smaller the particle size, the greater the potential health hazard. Control is exercised by the use of protective equipment and safe handling systems such as glove boxes, respirators, masks, air-handling devices, filters, etc.

In one embodiment, compositions of the invention may be prepared under conditions that prevent or minimize oxidation and/or reduction of the elemental metals (e.g., prevent or minimize exposure to humidity and/or oxygen (e.g., time and/or amount)).

Elements and alloys (that may contain these elements) that are useful to the formulation of elemental metal compositions of the invention may require special handling with precautions in finely divided forms determined by OSHA regulations. All may have respiratory exposure limits (due to irritation, but not biological toxins except at high doses of particulates or fumes) defined by OSHA for finely divided form. Certain elements may require special care due to skin irritation, known allergens, and may be absorbed (or cross) through inflamed skin, relatively low (HMIS ratings on flammability-will ignite as powder with a heat source, and health effects, environmental and chemical reactivity generally low HMIS #1 or less).

Mixing

Compositions of the invention may be mixed using any suitable method to obtain elemental metal(s) coated with sufficient coating material(s) in order to exhibit desirable field effect properties.

In some embodiments, additional materials may be added to an elemental metal composition to improve certain physical characteristics (e.g., malleability). For example an emulsifier such as lanolin may be added. Alternatively, other types of materials may be added, e.g., for stability, to prevent moisture, to prevent oxidation, to prevent microbial growth, etc. (e.g., sulfur, antioxidant(s), vitamin(s), other stabilizers).

In one embodiment, compositions may be prepared so that they are suitably malleable to be molded to fit a particular shape such as the individual shape of a subject's anatomical region that is to be treated (e.g., joint, back, etc.) or a plant feature. The composition may be molded during preparation to fit a form. Alternatively, the composition may be molded when applied to a subject or plant.

Activation

In one aspect, compositions of the invention may be prepared by including an activation step that increases the responsiveness of biological tissue when exposed to the activated composition. Examples of activation include heat (e.g., during or after mixing, or both), exposure to a source of electro-magnetic radiation (e.g., a Tesla coil); exposure to sunlight; exposure to the air; exposure to a source of ionizing radiation; exposure to electric current (e.g., by inserting electrodes into the composition and applying an alternating or direct current to the electrodes); exposure to a negative ion generator; etc.; or any combination of two or more of the above.

Ratios of Elemental Metals and Coating Materials

The ratio of elemental metal to coating material may range from 1:1,000 to 1,000:1 by weight or volume. However, higher, lower, or intermediate ratios may be used. For example, ratios of 100:1, 50:1, 10:1, 5:1, 1:1, 1:5, 1:10, 1:50, or 1:100 may be used. The appropriate ratio may depend on the nature of the metal (e.g., the size of the particles), the nature of the coating material (e.g., how waxy or oily it is), and the intended use (e.g., whether the composition is intended as a cream to be applied to skin or whether it will be provided in a container or a sealed device).

Preparations and Formulations:

Elemental compositions of the inventions may be formulated as creams, ointments, etc. In one embodiment, a cream or ointment may be manufactured based on a coated elemental metal preparation. In another embodiment, elemental metal(s) (e.g., particulate elemental metal(s)) may be added to an existing cream or ointment. The elemental metal(s) may be added in a coated form. Alternatively, the elemental metal(s) may be added without a coating and the components of the cream or ointment may act as a coating.

Suitable composition percentages of ointment mixtures may be determined for maximal biological or healing effect. However, each of the metals listed herein may have the capability to independently form a biologically active capacitor at many concentrations in combination with coating materials such as organic substances. Therefore, iron filings and ferrous metal sheets that are coated with organic substances also may become biologically active and can be shaped into many different useful applications. The overall effect of the surface area involved with metallic/organic interface and the capacitance of the substance in total appears to impact (and in some embodiments maximize) the biological effects.

In one aspect of the invention, an elemental metal composition may have non-linear or alternating properties (e.g., non-linear or alternating capacitance and/or field effects). In one embodiment, an elemental metal composition may be inducible (e.g., have increasing capacitance and/or field effect upon repeated exposure to an electrostatic or electromagnetic field).

Suitable formulations may be identified and used to preserve and/or enhance the non-linear, alternating, inducible properties of a composition of the invention. Certain formulations may be used to protect a metal from oxidation.

In some embodiments, a composition of the invention may be formulated with one or more additives (e.g., preservatives, anti-bacterial, anti-inflammatory, emulsifier, thickener, hardener, etc., or any combination thereof) in addition to the elemental metal and matrix components. In some embodiments, a composition may include an insulating, a corrosion resistant, and/or a hydrophobic or other water excluding material (e.g., in the form of the matrix or in addition to the matrix). The electrostatic and/or electromagnetic effects of one or more additives should be considered or assayed, and an appropriate amount should be used to prevent any unwanted effects.

It should be appreciated that a composition of the invention may include a homogeneous mixture of components (e.g., an evenly-distributed mixture). However, in some embodiments, a heterogeneous mixture of components (e.g., an uneven distribution) may be effective. The distribution may be evaluated, for example, using a microscope.

Containers:

In certain aspects, a composition of the invention may be provided in a container that is adapted to be contacted or exposed to an animal or plant surface. The container may be flexible, malleable, rigid, or include one or more flexible and/or malleable and/or rigid members or portions. In some embodiments, a container may be a sac, bag, or other flexible container. In some embodiments, an elemental metal composition of the invention may be wrapped or folded within a support material (e.g., metallic sheet, film, cloth, glass, etc.).

In one embodiment, a container may be shaped to fit onto a biological structure (e.g., anatomical feature).

In one embodiment, a container may include one or more features adapted for attachment to a biological structure. Examples of attachment features include belts, straps, hooks, etc. Alternatively or additionally, a container may be shaped to attach to a biological structure. For example, the container may be shaped as a cylinder, sheath, glove, sock, hat, etc. In some embodiments, the container may be shaped or designed to fit into an article of clothing (e.g., hat, glove, shoe, coat, etc.).

In some embodiments, a container may be shaped as a disc or sphere (e.g., a ball). In some embodiments, a composition of the invention may be shaped as a disc or sphere (e.g., a ball). For example, a disc or sphere may be between about 1 and about 5 inches in diameter. However, smaller or larger discs or spheres may be used (e.g., less than 1 inch, less than 0.5 inches, etc., or more than 1 inch, more than 5 inches, more than 10 inches, etc.). In some embodiments, a disc may be about 2 inches in diameter. A disc may be of any suitable thickness. For example, a disc may be between $1/10$ and 10 inches thick (e.g., about $1/8$, $1/4$, $3/8$, $1/2$, $5/8$, $3/4$, $7/8$, 1, 5, or more inches thick). However, thinner or thicker discs may be used. It should be appreciated that many other geometric shapes may be used (e.g., squares, rectangles, triangles, cubes, etc.). It also should be appreciated that a composition of the invention may be provided in a shape that roughly approximates a geometric shape. In some embodiments, a composition of the invention may be provided in a pad. In certain embodiments, a composition of the invention may be shaped to fit an anatomical feature (e.g., of a plant or animal, for example of a human) as described in more detail herein.

In one embodiment, a container may be adapted to receive one or more biological materials. A belt or item of clothing may be adapted to receive material, with or without a surrounding container material. The material may be provided in any shape. One or more separate packages (e.g., with or without surrounding container material) may be added to a belt, an item of clothing, furniture (e.g., chair, couch, bed, car-seat), sheet, or any other suitable support. For example, 1, 2, 3, 4, 5, 6, 7, 8, 9, 10, or more packages (e.g., discs, spheres, cubes, etc.) may be affixed or introduced into a single or separate spaces or pockets in a belt, an item of clothing, furniture, sheet, or any other suitable support. In some embodiments, several layers (e.g., 1, 2, 3, 4, 5, 6, 7, 8, 9, 10, or more layers) of an elemental metal composition may be separated by one or more layers of a support material (e.g., sheathing, for example fiberglass screening). In some embodiments, layers of compositions may be included between layers of different materials (e.g., solid metal foil, non-conducting felt, etc., or any combination thereof) to modify the intensity of a field effect (e.g., to enhance or reduce the effect).

A container may contain dry, sticky, waxy, and/or wet elemental compositions. Any suitable mass of an elemental metal composition may be used, for example, included in a container. For example, less than 1 g, 1-10 g, 10-100 g, 100-500 g, 500 g to 1 kg, 1-10 kg, 10-50 kg, or more material may be used (e.g., with or without a surrounding container).

In one embodiment, a container may be adapted to be mixed with biological materials (e.g., a pod or small container that can be mixed with seeds or fruit or vegetables or other biological materials).

In one embodiment, a suitable storage container may be used to preserve or maintain an electrostatic charge and/or an activated state of an elemental metal composition.

A container may be manufactured from any suitable material (e.g., glass, cotton, wool, silk, metals, plastics, wood, synthetic fibers, natural fibers, polymeric material, resins, etc.).

In some embodiments, a container may be of a material that is untreated (e.g., that has not been treated with a chemical additive, bleaching agent, preservative, dye, paint, fire retardant or other chemical adulterant or treatment that may alter the electrostatic and/or electromagnetic properties of an elemental metal composition). For example, in some embodiments, a container does not include (e.g., does not include a significant amount of, for example less than 50%, less than 40%, less than 30%, less than 20%, less than 10%, less than 5%, less than 1% by weight or volume of) a material that reduces the electronegative properties of an elemental composition (or that results in an electropositive effect). In some embodiments, plastic containers (e.g., polyethylene and/or polypropylene plastic containers) are not used for medical or therapeutic (e.g., analgesic) compositions or devices of the invention. Certain containers may be used to protect a metal from oxidation. In some embodiments, a container may include a dessicant. In certain embodiments, a container may be air-tight and/or provide a moisture barrier.

Applications:

Animal Applications

Aspects of the invention include therapeutic applications for animals. For example medical applications in human include treatments of skin conditions (e.g., psoriasis, skin cancer or pre-cancerous conditions such as hyperkeratotic lesions, melanomas, etc.). As used herein, treating, or treatment, or treat, refer to a therapeutic prevention, cure, reduction (e.g., in time and/or intensity), and/or delay of symptoms associated with a disease, condition or injury. Accordingly, aspects of the invention provide methods for treating one or more injuries (e.g., lacerations, bruising, soft tissue injuries, bone fractures, burns) and pain (e.g., joint pain, neuromuscular pain, and other forms of pain). Joint or bond pain may include pain in one or more of the following: an anatomical feature, a joint, a bone, a spine or portion thereof (e.g., a foot, an ankle, a hand, a wrist, a knee, an elbow, a hip, a shoulder, a lower back region, an upper back region, a shin, a neck, etc.). Compositions of the invention may be used for similar applications in veterinary care for animals such as pets and farm animals. An animal may be a vertebrate, such as a bird, a fish, or a mammal, e.g., a mouse, cat, dog, rat, hamster, cow, pig, horse, goat, sheep, rabbit, etc.

In one embodiment, a composition of the invention may be included with an implant or other device that is surgically inserted into a body (e.g., a human body). The composition may be coated on the surface of the implant/device or it may be encased within the body of the device or within one or more containers that are inserted into the body in proximity to the implant or device. For example, compositions of the invention may be used with implants for joint repair, non-union fracture repair, etc.

Other medical and/or veterinary uses may include: anti-pruritic; analgesic; anti-hyperplasia; anti-inflammatory; anti-infective; anti-mycotic; anti-microbial; anti-viral; anti-neoplastic; anti-proliferative; anti-psoriatic; anti-photo aging; anti-rheumatic; anti-arthritic; wound healing; augmentation of grafts and implants; inclusion in containers to preserve transplant organs; insect bite healing; treatment of warts; treatment of burns; treatment of sun burns; treatment of abrasions; treatment of ulcers; to improve healing of trauma; and/or to improve or treat any other skin condition (e.g., acne, etc.). Aspects of the invention may be used to treat inflammation, swelling and/or itching (e.g., reduce the intensity and/or duration of pain and/or itching) due to environmental, animal, or plant exposure. For example, aspects of the invention may be used to treat, prevent or reduce a response to an allergen or toxin (e.g., after exposure to animal hair or dander, pollen, animal venom, plant or animal toxin, poison ivy, poison oak etc.). Aspects of the invention may be used to treat pain or discomfort associated with a disease or condition (e.g., cancer, inflammation, tissue degeneration, injuries, fractures, arthritis, rheumatoid arthritis, osteoarthritis, a degenerative etiology of pain, a discogenic disease, etc.). In some embodiments, aspects of the invention may be used to provide analgesic relief for one or more conditions. For example, analgesic relief may be provided for Osgood Schlatter's Disease, Patella-Femeral syndrome, and/or Chondromalacia. In some embodiments, compositions and devices of the invention may be used to relieve pain associated with growth (e.g., in children) or associated with tissue degeneration (e.g., associated with aging). In some embodiments, compositions and devices of the invention may be used to treat regular pain (e.g., pain associated with menstrual cramps), seasonal pain or inflammation or irritation, or sporadic pain or inflammation or irritation.

Depending on the application, the elemental metal composition may be used in a different suitable configuration (e.g., paste, cream or ointment, layered configuration, container, sheath, etc.). A composition (e.g., a composition enclosed in a container) may be molded to fit an individual body part. The amount of composition that is applied may be tailored to a particular application. For example, a composition in a cream (or past or ointment) form may be applied in a sufficient amount to cover an affected area of skin or an area covering a joint or other bone or body part that is in need of treatment. If the composition is enclosed in a container, a sufficient amount should be used so that the effects of the material can reach to the desired area of treatment. The amount of material may, in part, be determined by the size of the enclosure. Accordingly, different amounts of material may be used (e.g., from several grams to several kilograms, for example, about 5 g, 10 g, 20 g, 30 g, 40 g, 50 g, 100 g, 250 g, 500 g, or 750 g). However, smaller or larger amounts may be used. Similarly, the duration of exposure may be tailored to a particular application and also may be determined by the user. For example, if a desired result is obtained (e.g., pain relief) a subject may discontinue use. In other embodiments, a subject may be exposed on a regular basis (e.g., every day, once a week, etc.) to a suitable composition. In one embodiment, a subject may be exposed at night. For example, a suitable composition may be applied at night or incorporated into a bedding material (e.g., a pillow, blanket, mattress, other suitable enclosure, an animal bedding material, etc.). In addition, or alternatively, a subject may be exposed during the day. For example, a suitable composition may be included in clothing material (e.g., pants, shirts, skirts, coats, gloves, hats, shoes, socks, etc.). In one embodiment, a composition may be provided in an enclosure that can be attached to, or placed in, an item of clothing (e.g., in a hat, glove, shoe, pocket, etc.).

In other embodiments, a composition of the invention may be included in a bandage (e.g., included in a pad in a bandage such as a band-aid) or other material that is used to wrap or cover a wound or painful area of a body.

In certain embodiments, a composition may be formed into one or more separate shapes that can be inserted into container, a pocket, or sewn into a belt or other support. For example, a belt may include one or more discs of material (e.g., 1-5, 5-10, or more).

An animal surface (e.g., skin) may be exposed to a composition of the invention directly or indirectly (e.g., in a container or through clothing, bedding, or furniture) for any suitable period of time (e.g., 1-5, 5-10, 10-30, or longer), one or more hours (e.g., 1-5, 5-10, or longer), one or more days (e.g., 1, 2, 3, 4, 5, 6, 7, 8, 9, 10, or more), one or more weeks (e.g., 1, 2, 3, 4, 5, 6, 7, 8, 9, 10, or more), one or more months (e.g., 1-5, 5-10, or longer) or one or more years (e.g., 1, 2, 3, 4, 5, etc.). In some embodiments, a animal may be exposed to an elemental metal material on a regular and/or seasonal basis (e.g., every, spring, summer, fall, winter, or any combination thereof) depending on the application and/or the condition being treated.

Plant Applications

Aspects of the invention include plant applications. Compositions of the invention may be used to alter one or more aspects of plant physiology (germination, growth, flowering, ripening, decaying, etc.). Compositions of the invention may be used in connection with any plant tissue, including, but not limited to, seeds, roots, branches, fruits, vegetables, etc. In some aspects, a composition of the invention may be applied directly to plant material (e.g., in the form of a cream, oil, or other similar substance). In other aspects, a composition of the invention may be provided in a container or sheath that can be contacted with plant tissue, structure, or cells (e.g., roots, sterns, branches, leaves, seeds, flowers, etc.). For example, a composition of the invention may be provided in bags or solid containers that can be included with seeds (e.g., in seed silos, sacs, etc.) in order to enhance germination (e.g., to speed up germination, to increase the percentage of seeds that germinate, etc., or any combination thereof). In one embodiment, seeds may be stored with a device of the invention. In another embodiment, a device of the invention may be added to seed containers when germination is desired (or for example several weeks prior to germination or before seeds are sowed). In one embodiment, seeds may be coated directly with a composition of the invention. A composition of the invention may be used as a seed or soil "amendment." In one embodiment, one or more elemental metals (e.g., particulate elemental metals) that may be coated (e.g., with a non-conducting or semi-conducting material) or non-coated may be added to an existing seed or soil "amendment" that contains one or more other active ingredients. In one embodiment, a container or surface (e.g., a table) may include one or more layers of coated elemental metal(s) of the invention (e.g., 2, 3, 4, 5, 6, 7, 8, 9, 10, or more layers). Plant material (e.g., bulbs, seeds, seedlings, small plants, large plants, vegetables, fruit, etc.) then may be contacted with the biologically active composition by putting the plant material in the container, on the table, or near any other suitable device that contains a biologically active composition of the invention. In yet other embodiments, a device (e.g., a weather resistant device) may be placed on or near a plant growing inside (e.g., in a house or a greenhouse) or outside (e.g., in a garden, field, or forest) or in water (e.g., in a tank, pond, lake, river, sea, ocean, etc.).

In other aspects, an elemental metal composition of the invention may be added, either directly or in a suitable container, to agricultural/horticultural products such as soil (e.g., top-soil), mulch, fertilizer, insect or other pest control compositions, etc. In some embodiments, an elemental metal composition of the invention may be applied to the inner surface of a container (e.g., a vial, beaker, vase, vat, silo, etc., or any combination thereof) that will be used to store, germinate, and/or grow seeds and/or other plant material. In some embodiments, a formulation of the invention may be included in a seed tray, a growing platform, or other surface or container. In some embodiments, a composition of the invention may be covered or contained within a material that does not reduce the electro-negative properties of the material or result in an electro-positive environment. In some embodiments, plastic (e.g., polyethylene and/or polypropylene plastic) is not used as a coating or encasing material.

In some embodiments, a composition for use with a plant may include one or more elemental metals that are plant nutrients (e.g., micro- or macro-nutrients essential for plant growth). Examples of macronutrients include: N, K, Ca, Mg, P, and S. Examples of micronutrients include: Cl, Fe, B, Mn, Zn, Cu, Mo, and Ni.

Accordingly, aspects of the invention may be used to improve food storage and/or transport; to improve seed and/or grain germination; or to improve fruit, grain and/or seed yield. Aspects of the invention may be used in connection with any plant or seed, for example any agricultural plant or seed (e.g., barley, corn, cotton, rice, soy, wheat, lettuce, tomatoes, potatoes, apples, oranges, pairs, bananas, etc.) or any flower plant or seed.

As described above for medical applications, large or small amounts of material may be used and may be exposed to plant material for relatively short or long periods of time depending on the application and the desired result. In some embodiments, a seed or plant may be exposed to an elemental metal composition for one or more minutes (e.g., 1-5, 5-10, 10-30, or longer), one or more hours (e.g., 1-5, 5-10, or longer), one or more days (e.g., 1, 2, 3, 4, 5, 6, 7, 8, 9, 10, or more), one or more weeks (e.g., 1, 2, 3, 4, 5, 6, 7, 8, 9, 10, or more), one or more months (e.g., 1-5, 5-10, or longer) or one or more years (e.g., 1, 2, 3, 4, 5, etc.). In some embodiments, a seed or plant may be exposed to an elemental metal material on a regular and/or seasonal basis (e.g., every, spring, summer, fall, winter, or any combination thereof).

It should be appreciated that suitable amounts of material and/or durations of exposure may be optimized by comparing results for animals or plants exposed to different amounts (e.g., including a placebo control), and/or durations of one or more different types of elemental metal compositions with or without containers (e.g., using one or more different types of containers). The effectiveness of an exposure may be evaluated statistically. In some embodiments, an exposure of the invention (e.g., a combination of type and amount of material, container, and/or duration or exposure) is designed to be an amount sufficient to have a statistically significant effect. In some embodiments, the effectiveness of a therapeutic composition may be evaluated in a double-blind placebo-controlled trial. In some embodiments, the effectiveness to treat pain or inflammation may be evaluated by obtaining average patient reports (e.g., using a pain scale, for example a 0-10 Lickert type scale) relative to a control on a daily, weekly, monthly, or other time-dependent basis and evaluating them using one or more statistical tests. In some embodiments, a patient quality of life score (e.g., related to activity and/or mobility) may be used to evaluate effectiveness. In some embodiments, the average amount of medication used over a certain time period (e.g., a week, a month, or longer) may be evaluated to determine if a treatment is effective.

It should be appreciated that for medical, veterinary, and/or plant uses, a composition of the invention may be combined with one or more other compositions or preparations that are used to treat or enhance an animal or plant biological process. In some embodiments, a composition of the invention may be sterilized. In one embodiment, a composition may be prepared from sterile materials. In one embodiment, a composition may be sterilized after preparation or during preparation (e.g., by heating, irradiation, etc.).

It should be appreciated that in some embodiments, a composition of the invention may have a limited period of effectiveness (e.g., a period during which a useful electronegative or electropositive effect is maintained). Accordingly, certain compositions of the invention may be disposable an or rechargeable. For example, an elemental metal composition may be rechargeable as described herein. In some embodiments, a container described herein may be refillable (e.g., with freshly produced or recycled elemental metal material).

It also should be appreciated that compositions of the invention may be useful to alter growth, differentiation, or other properties of biological materials ex vivo or in vivo (e.g., to enhance plant, animal, or microbial cell growth in vitro, to preserve organs such as organs for transplantation, to preserve plants or plant grafts for transport, etc.).

These and other aspects of the invention are illustrated by the following non-limiting examples.

EXAMPLES

Example 1

The effectiveness of metal containing skin ointments was tested on psoriasis, hyperkeratosis (pre-cancerous skin lesions), and for joint and neuromuscular pain management.
Materials Used:

Iron powder (degreased purified form, e.g., from J.T. Baker Iron, Powder #2226-01 Fe FW 55.85, assay purity of 97.0% [Mallinckrodt Baker, Inc. Phillipsburg, N.J. 08865, PH. 908-859-2151, ccas no. 7439-89-6]) was found to be more effective than iron filings.

Zinc Metal Dust (e.g., lab grade, FW 65.39, highly pulverized-refined form of powder, e.g., from Post Apple Scientific, Inc., 8893 Gulf Road, North East PA., 16428, lot # 030701-15m) also was found to be more effective than metal filings.

Bees Wax, natural formulation with no added chemicals such as preservatives, scents or dyes, only filtered, with melting point of 143 degrees F. (e.g., from Yaley's candle crafting enterprises, Inc. Lot No. 110016) was used to coat the elemental metal(s).

Liquid Lanolin, natural formulation derived from sheep's wool, with no added chemicals such as scents, solvents, preservatives, or dyes. (e.g., from Now Foods, Bloomingdale, Ill. 60108, code 7730) was used as an emulsifier.
Ointment Composition (by Weight):

An ointment with the following composition was prepared and tested.
Fe 29.6%
Zn 25.6%
Bees Wax 25.6%
Lanolin 19.2%
Ointment Mixture Preparation:

The amount of organic substance (e.g., wax) used was based on the minimum amount of material needed to coat all the particles of metal (based on a visual analysis of the preparation). The wax metallic mixture is not malleable at room temperature and is easier to use with a lubricant that is both stable and that does not interfere with or disrupt the wax-metallic interface, but enables the mixture to become malleable and remain stable to moisture.

The tested substances seem to loose their biological reactivity when they are wet, but resume their activity when dried again.

The percentage of lanolin that was used was sufficient to make the wax-metallic mixture malleable and of paste-like consistency. This percentage may very depending on the viscosity of the lanolin used and the desired consistency of the product. It should be noted that lanolin and bees wax may have bacteriostatic as well as enzymatic activities that function indirectly as preservatives, emollients (like petroleum jelly), and anti-inflammatories. However, these additional activities are not required for the therapeutic properties of the invention. For example, these additional activities may not even be involved in a biological process when a composition of the invention is applied in a bandage or therapeutic patch that has no direct contact with the skin or body tissues of a subject.

The composition described in this example is a non-irritant, non-toxic, and apparently benign substance with little if any anticipated side effects (with the exception of a known allergy to bees wax and/or lanolin). The metals in their native form may be toxic if inhaled, but benign in the formulation described herein due to its consistency and stability.

Method of Formulation:

Iron and zinc materials were measured by weight and mixed in a stone worker's tumbler or vibrational mixer, until thoroughly mixed.

Wax and lanolin were measured and added to the tumbler along with the metallic substance and mixed until forming a thick paste. This mixing process may take several days depending on the speed and effectiveness of the tumbler apparatus.

Application:

The ointment described in this example can be applied directly to human skin as a treatment for psoriasis. The paste is placed on the skin and an occlusive dressing is placed over the ointment to maintain its contact with the skin. Effective results were observed with an exposure time of around 6-8 hours per day for up to several weeks. Up to 12-16 weeks of exposure may be required for restoring normal integrity of human skin. If scarring has occurred due to the psoriasis lesion, the skin retains the scarring, at least to some extent. The treatment appeared to be very effective when the ointment was replaced/refreshed daily and a new covering was applied exposing the skin surfaces to treatment for 24 hours/day daily. Under these circumstances, the length of treatment was reduced several fold to perhaps 4-6 weeks. It is anticipated that in some circumstances treatment may need to be continued for longer periods of time (e.g., for months, years, or indefinitely) for at least at short time (e.g., a pre-determined minimum number of hours) per day in order to sustain normal skin architecture.

Occlusive Dressings:

An occlusive dressing was used to keep the material on the skin surface when the ointment was placed directly on the skin. This prevents moisture penetration that may decrease the effectiveness of the ointment treatment. Wool (e.g., 100%, natural felt, with no chemical additives) was particularly effective (it may sustain a negative static electrical charge). Cotton was less effective. Silk did not show any significant effect when tested in psoriasis. However, silk may be used for different compositions and/or applications. Plastics may be used but may not be as effective as cloth (wool or cotton) bandaging or ferrous metals in situation when a positive charge is desired due their reduced ability to hold a positive charge. Adhesive tape such as athletic tape may be used to secure the bandage. Pre-manufactured band aids using one of many available over-the-counter materials have been shown to be effective.

Another bandage design may be more appropriate when the skin integument is disrupted with open lesions, or if the individual does not want to apply the ointment directly to the skin (e.g., for aesthetic reasons). An alternative design may use a contained ointment patch made of stainless steel foil (e.g., with the edges wrapped in wax and adhesive athletic tape to prevent a sharp-lacerating edge). In other configurations, multiple layers (e.g., up to 15 layers or more) of metal foil covered with a thin layer of an ointment may be more effective than single layer. Without being bound by theory, it is expected that the increased energetic capacitance of the layered materials may have an increased therapeutic effect.

Compositions described in this example were found to be effective when layered using the following stainless steel sheets: Austenitic grade #321, which is an annealed stainless steel of thickness 0.003", and also contains a minimum of 12% chromium, as well as small amounts of titanium and nickel. Stainless steel was chosen based on its relative inert interaction with skin secretions. In addition, stainless steel i) can be washed and/or sterilized if soiled, ii) does not rust (which renders the ointment/paste biologically inactive), and iii) appears to hold a charge. It is expected that numerous forms of sheet steel and sheet stainless steel of many different chemical and crystalline compositions may be used. It is expected that higher carbon stainless steel such as #302, and #303 (with sulfur) also would be biologically active and may be even more active than #321.

Potential Ointment/Paste Applications:

Skin Applications

A number of different skin conditions were tested and found to benefit from treatment with an ointment described in this example.

Psoriasis was observed to respond to direct ointment application or an occlusive patch dressing using wool, cotton, or stainless steel foil coverings in single or multiple layers. Visible changes in the psoriatic lesions were observed.

Pre-cancerous/hyperkeratotic lesions were observed to respond to a direct ointment application or an occlusive patch or dressing using felt (e.g., wool felt), wool or stainless steel coverings in single or multiple layers. Visible changes in hyperkeratotic lesions were observed.

Wound healing seemed to be accelerated by a composition described in this example (e.g., cuts and bruises healed faster when exposed to a composition described in this example).

Several second degree burns were observed to respond to exposure to a composition described in this example. For example, significant pain relief was obtained for a second degree burn caused by steam under pressure when treated with the metallic form of occlusive dressing. Cooking burn and finger tips from a hot light bulb all responded to direct ointment with occlusive dressing, stainless steel dressing, and/or band aid dressing, resulting in an analgesic effect and an apparent acceleration of healing with reduced sloughing of skin.

Pain Management

Pain relief in musculoskeletal injuries and overuse syndromes were tested and demonstrated by decreased pain of a triple bone fracture when the ointment/paste was placed in a quarter inch think pad, made from felt covered paste wrapped around the fracture area for overnight use and one hour treatment periods. Significant pain relief was also tested and demonstrated in neuromuscular pain of a rotator-cuff tendinitis and temporary bruising using one hour treatment periods with the same pad/formulation described above. Numerous shapes and sizes of such a pad can be manufactured for different applications, e.g., for orthopedic splints and braces for any joint or limb.

Pain relief in arthritis (osteoarthritis) was tested and demonstrated by increased mobility, agility and overall activity level in an elderly dog treated with a full body sleeping pad constructed with the paste/ointment inside a stainless steel foil pad described above.

Example 2

The effectiveness of compositions containing several mixtures of iron, zinc, aluminum, and/or copper were tested.
Composition Formula:

Compositions containing combinations of iron, zinc, aluminum and copper were tested. It is expected that finer dusts (200 mesh or higher) will produce greater biological effects due to the increased surface area of the metal/organic interface. Finer metal dusts were used (e.g., produced using 325 mesh) and were very effective.

Iron and zinc were used at about the same ratio (iron 29.6% and zinc 25.6%) for most experiments, and aluminum and copper were added up to 10% of total weight of metals. It was observed that aluminum and copper dust in relative concentrations of up to 10% of the weight of iron and zinc contributed to the effectiveness of the compositions. Other concentrations of aluminum and/or copper may be more effective for certain applications (e.g., different conditions and or organisms). Based on the present description, one of skill in that art can test other concentrations and identify useful and/or optimal ratios of different metals for different applications.

It is expected that gold, silver and/or platinum dust also may be biologically active when used as the metals, or when combined with other metals in compositions described herein.

It should be appreciated that lanolin is useful primarily as an effective emulsifier to facilitate the pliability of the compounds at room temperature, and may be especially useful for applications to skin surfaces. However, lanolin may not be suitable or optimal for other applications described herein. Lanolin does not appear to have a significant effect on the biological properties of a composition of the invention when wax or some other carbonaceous material is used to coat the metal particles. It was found that wax and beeswax alone with the metallic substances yielded effective biologically active compounds.

Example 3

Different methods of manufacturing biologically effective compositions were tested.
Room Temperature Mixing:

A rock and mineral tumbler was used to mix shards of wax, lanolin and the selected metals. This mixing was continued for several days. This mixing yielded an oily mixture that was easily pliable. This method does not maximize the mixing and coating of the metallic substances. However, this method is simple and the resulting compounds were biologically active.
Heating and Mixing:

The wax was heated to a liquid form, approximately 145 degrees F., without overheating or chemical breakdown of the wax. Each metallic dust component was heated separately using a natural gas or propane/acetylene torch until the metal reached the heat of incandescence.
The metals were plunged into the liquid wax one component at a time. Each metal was heated separately, because incandescence is reached at a different temperature for each metal and the temperature was kept below the temperature of vaporization for each metal. Metal was then cooled so that wax was not brought to boiling temperature. The metals then were stirred mechanically together with the molten wax, and allowed to cool to room temperature.

If the resultant material is to be pliable at room temperature, lanolin (or petroleum jelly, etc.) may be added. Lanolin may be added, for example, in an amount that is equal to the weight of the wax that is used. However, different amounts of lanolin may be used as long as there is enough carbonaceous material/wax to coat a sufficient percentage of the metallic particles to produce a composition with certain desired biological properties.

Compositions of the invention produced by heating and mixing were found to be more biologically active than compositions produced by room temperature mixing.

Without wishing to be bound by theory, it is thought that heating the metal particles to incandescence may alter their surface architecture in such a manner as to increase their surface area available for coating and also may alter their electrical characteristics in such a manner as to increase their static capacitance. However, improved mixing of the metal particles and the wax may contribute to the increased effectiveness of compositions that are made by heating and mixing.

Accordingly, other methods that alter (e.g., increase) the surface area of metal particles and/or alter (e.g., increase) the mixing and/or coating of the metal particles with the coating material are expected to alter (e.g., increase) the biological properties of compositions of the invention. Using the present description, one of ordinary skill can identify and select appropriate methods for preparing compositions of the invention with desirable (e.g., optimal) properties for a particular application and/or organism.

Example 4

An elemental metal composition of the invention may be activated (e.g., treated in a way that increases its ability to be charged) by activating the elemental metal(s) before and/or after mixing with a suitable coating material. Activating may be achieved, for example, using one or more of the following methods, heating (e.g., heating the metal and/or composition to incandescence); exposing the metal and/or composition to an electrostatic field (e.g., a Tesla coil); exposing the metal and/or composition to friction; exposing the metal and/or composition to sunlight; and/or other suitable activating methods such as exposure to air or to a negative ion generator.

Activating may be performed during the manufacturing process, and/or after the composition is manufactured. For example, charging/activating may be performed before and/or after packaging, and/or before and/or after storage, and/or before and/or after first use, and/or before and/or after any subsequent use.

Example 5

Compositions of the invention were used to treat chronic osteoarthritis of the cervical spine, chronic post traumatic pain of the rotator cuff, and post surgical (spinal stenosis) lumbosacral pain, with complications of distal digital extremity relative anesthesia.

A 78-year-old woman (subject) has a five-year history of degenerative joint disease (osteoarthritis) in both the lumbosacral and cervical spine and left rotator cuff, the latter due to an old injury. Subjective symptoms include chronic, end of day pain, radiating in her left arm and leg, and relative anesthesia in her distal left foot and toes as well as in the ulnar nerve projections (smallest two fingers) of her left hand. Subject requires daily oral non-steroidal anti-inflammatory medication and Tylenol as well as daily physical therapy and exercise to diminish her symptoms of pain. The anesthesia is chronic and unchanging.

A 6 inch by 12 inch, ½ inch thick pad of compound was prepared (mixture components: 30% iron, 20% zinc, 10% copper, 10% aluminum, wax 25%, petrolatum 5%), knitted together with aluminum screening (to give the pad structure and act as a conductor), which was enclosed in a fiberglass mesh and then covered by wool felt and an inner layer of worsted wool (to keep the oily material from breaking apart and "bleeding through"). This pad was placed on a chair behind her lumbar region where she sat. As well as compound "discs" made with the same metals and just wax (no petroleum or lanolin so it is firm at room temperature). These "discs" were less than ½ thick and 3 inches by six inches, and then "shaped" through warming on a heating pad to snug "fit" over her neck and shoulder. These fitted discs were placed in cotton sleeves and wrapped over the cervical neck region and shoulder.

An experiment began at 4 PM, the usual time of onset of symptoms. To our pleasant surprise, the subject reported within 45 minutes of application her shock that sensations were returning to the usually anesthetized toes and fingers, (the restored sensations have continued intermittently since the onset of the experiment as long as the subject continued to use the apparatus). Sensation returned to relative anesthesia when the experimental protocol was stopped. The subject also reported a delay and decrease of intensity of her end of day pain more in her leg than arm. She continued to use the pads for 3-4 hours and found she did not "run" to the medicine cabinet for her pain medications, and took half her usual amount of medication over the following weeks of experimental use of 3-4 hours of daily use minimum.

Example 6

Compositions of the invention were used to treat an 85-year-old man with a ten-year history of metastatic prostate cancer known to have osteo-metastatic lesions throughout the body. The subject complains of posterior cervical neck pain with some radiation down the arms for six months duration. We do not know if the source of this pain is carcinogenic, or degenerative arthritic or discogenic. He placed discs of the formulation as described above in the form of "discs within cotton" cloth to hang over the painful neck region 4 hours daily. He noted no particular changes in pain symptoms or analgesic medication usage for two weeks. At the end of the two-week experimental period he noted the pain somewhat quickly disappear over a few hours. The pain reportedly has not returned for at least eight subsequent weeks. He has discontinued regular pharmaceutical analgesic usage for his cervical pain.

Example 7

The physical properties of a composition of the invention (e.g., capacitance; electrostatic field effect; electromagnetic field effect; charge; etc.) may be measured using any suitable method. The measured physical properties of a composition of the invention may be used to evaluate its biological effectiveness and determine which application(s) it may be suited for. In addition, the measured physical properties of a composition may be used to determine how to modify a composition to change its physical properties and adapt it for a particular biological application.

The following non-limiting method was used to measure electrostatic properties of certain compositions of the invention.

Electroscope Measurement Protocol:

A Kolbe type "rigid arm pointer" electroscope was used with a terminal with cross bores for 4 mm plug and case earth grounding. Scale segments were marked for timed measurement of "discharge time" per segment with a stopwatch. A specific segment was chosen for each series and comparison measurement consistent with the electroscopes capacity to hold a charge for the conditions of the environment at that time.

Stopwatch measurements were taken visually with elapsed time unknown to the operator at initialization and termination of each specific segment time measurement. Experimental use of this protocol under control conditions resulted in an experimental error of less than 10%.

A Plexiglas rod rubbed on human hair was used as a source of charging with "negative" static electrical charge.

Known parameters that affect electroscopic discharge rate include the time of day (diurnal variation), the season of the year, ambient conditions such as ambient humidity, current weather conditions, as well as the electrodynamic effects of any electronic equipment that may induce local fields.

To minimize experimental errors caused by these parameters, the following measurements were obtained contiguously, and all test compound data (e.g., inert-wax, iron, zinc and active-compound, etc.) were compared with other data obtained immediately after each other measurement rather than with data from another time or day.

Measurement Data:

Indirect electrostatic and direct electrostatic field effects were measured for two compounds: compound #3 and compound #5. Compound #3 contained, 29.6% iron, 25.6% zinc, 25.6% beeswax, and 19.2% lanolin (all as a % weight). Compound #3 was prepared by tumbling at room temperature for a week (using shredded wax and the other components). Compound #5 contained, 30% iron, 25% zinc, 25% beeswax, and 20% lanolin (all as a % weight). Compound #5 was prepared by melting the beeswax and adding the lanolin and iron/zinc mixture and mixing until solidified.

Indirect Electrostatic "Field Effect"

A composition of the invention was placed on a felt-backed wire structure surrounding the electroscope body and the discharge was compared to ambient discharge:

Trial # 1. Trial ambient: test material (average of three readings each):
  Ambient-without test material: 116 seconds
  With test compound # 3: 144 seconds
  The results show a 24% increase in discharge time due to the "field effect" of substance # 3.

Trial # 2. Trial ambient conditions: compound #3: inert bees-wax:
  Ambient-without test material: 627 seconds
  With compound # 3: 1321 Seconds
  With inert bees-wax: 740 seconds
  The results show a 111% increase in discharge time due to the "field effect" of compound # 3.

"Direct Electrostatic Effect"

An aluminum electrode was placed into the same volume of compound or inert material "directly" (conductive contact with electroscope electrode) and the other end of the aluminum electrode was placed into the electrode pole of the Kolbe electroscope, thereby measuring comparative discharge times of the same segments continuously over time.

Trial # 1. Comparing the discharge times of compounds #3 and #5:
  Compound #3: 64 seconds
  Compound #5: 31 seconds
  The results show that compound # 3 discharge time is 106% greater than compound # 5 immediately after compound # 5 is manufactured.

Trial # 2. Comparing the multiple trial charging characteristics of pure bees wax versus the charging characteristics of compound # 5:

Wax discharge time remains the same over multiple (2) charge and discharge events.

Compound # 5 increased discharge time by 172% with second (2) charging cycle.

Trial # 3. Comparing the multiple trial charging characteristics of pure bees wax versus the charging characteristics of compound # 5:

Wax discharge time remains within 10% of its own discharge time over multiple (6 times) trials of charging and discharging.

Compound # 5 increases discharge time of 398% over its own original discharge time with multiple (6 times) charging and discharging.

Trial # 4. Comparing the charging characteristics of pure Iron and Zinc dust alone:

Iron dust (21 seconds)

Zinc dust (43 seconds)

The results show that iron discharges about twice as fast as zinc. However, discharge is stable over multiple charging and discharging cycles of both compounds.

These results show that compounds with biological activity are characterized by a measurable field effect as evidenced by an increase in "static electrical tension" when the electroscope discharge time is quantified. Compound # 3 and #5"s "electrical tension" is greater than the natural environmental and inert beeswax discharge time. This can be demonstrated through an indirect field effect and through a direct electrical connection with the Kolbe electroscope.

In certain embodiments of the invention, compounds may be exposed to an "activation" process after manufacture in order to obtain an energetic effect. Activation may occur spontaneously over time, with the application of a secondary electrostatic charge, and/or through interaction with a biological system. This "activation" was illustrated through direct electrostatic measurements of compound # 3 discharge time that was 52% greater than compound # 5 immediately after compound # 5 is manufactured. Measurements taken immediately after manufacture (in the absence of an activation step during manufacture) did not show any significant differences in electroscopic charge characteristics. Accordingly, certain compositions may become charged over time.

The results also show that compounds of the invention may have an electrostatic charging property of "increasing" capacitance with serial cycles of "charging and discharging." This property was not observed for any of the primary substances that were used to prepare the active composition. The primary (inert) substances showed a stable capacitance with serial cycles of "charging and discharging."

Example 8

Compositions of the invention may be added to poultices, ointments, or other preparations in order to enhance their therapeutic effects.

In one embodiment, a poultice is a raw or mashed herb applied directly to the body (it may be applied wet directly to the body) or encased in a clean cloth and then applied. Poultices are used, for example, to heal bruises, putrid sores, soothe abrasions, or withdraw toxins from an area. They may be applied hot or cold, depending on the health need. Cold poultices (and compresses) may be used to withdraw the heat from an inflamed or congested area. A hot poultice or compress may be used to relax spasms and for some pains. To make a poultice, fresh or dried herbs that have been soaked in boiling water until soft may be used. They may be mixed with enough slippery elm powder to make the poultice stick together. The poultice may be placed on an affected body part that is then wrapped with a clean cloth. According to aspects of the invention, elemental metal(s) and/or coating(s) of the invention may be mixed with the poultice during and/or after poultice preparation in order to produce a poultice that also has a therapeutic "field effect." In one embodiment, the poultice preparation itself may be sufficient to provide a coating according to aspects of the invention.

In one embodiment, an ointment is a soothing, healing, slightly oily or fatty substance into which the essence of a healing plant has been dissolved. This may be accomplished by heating the fat or oil with the plant until it loses its normal color and the oil or fat has absorbed the healing chemical principles. The plant then may be strained out. Preservatives such as drops of tincture of benzoin, poplar bud tincture, or glycerin are optional additions. Ointments may be prepared in small batches and kept tightly closed with paraffin wax so that they don't decompose. Pork lard is a traditional folk, herbal, and pharmaceutical base for ointments. It may be purified by simmering and straining. It may have healing abilities even without the addition of herbs, like many fats and oils. Purified, liquefied anhydrous lanolin also may be used as a base for ointments. Lanolin is a substance washed from the wool of sheep. It is available in many levels of purity and its properties may vary depending on the product. This oil may be considered to be the closest to skin oil. Almond oil, cocoa butter, wheat germ, and vitamin E may be used as neutral bases for ointments. In some embodiments, VASELINE® (Conopco, Inc. d/b/a Unilever) may be used. Any of the oils/fats described herein may be used alone or in combination. Ointments typically contain at least one substance that can thicken the final product. Lanolin may be used as a thickener. Similarly, cocoa butter may be used as a thickener. However, other thickeners may be used. For example, other thickeners may be glycerin, honey, liquid lecithin, etc. However, these thickeners are stickier than lanolin or cocoa butter. Alternatively or additionally, various powdered resins and/or gum may be used to thicken an ointment. They typically swell up when first soaked in cold water and then simmered in gently boiling water (after which they may be added to a preparation). Other thickeners may be agar-agar, Irish moss, seaweed thickeners, etc. Fruit pectin (e.g., from green apples) also may be used (e.g., alone or in addition to one or more other thickeners), for example, to thicken creams and ointments. An ointment also may include one or more hardeners in addition to thickeners. Beeswax is a useful hardener. Paraffin wax also may be used (alone or in combination with beeswax and/or other hardener). According to aspects of the invention, elemental metal(s) and/or coating(s) of the invention may be mixed with the ointment during and/or after ointment preparation in order to produce an ointment that also has a therapeutic "field effect." In one embodiment, the ointment preparation itself may be sufficient to provide a coating according to aspects of the invention.

It should be appreciated that in addition to, or instead of, the poultice or ointment components described above, other natural and/or synthetic components may be used to prepare poultices or ointments of the invention.

The invention claimed is:

1. A non-conducting composition for relieving pain, comprising substantially water-free particles of elemental iron, zinc, copper, and aluminum having an average diameter of less than about 100 microns, distributed within and separated by an insulating matrix substantially free of air pockets and comprising petroleum jelly, lanolin, silicone, wax, or combinations thereof, wherein the composition is non-conducting, wherein the distribution and separation of the particles within the matrix imparts capacitance into the composition, and wherein the capacitance of the composition alters an electrostatic field, an electromagnetic field, or both an electrostatic and an electromagnetic field of the human body or the body of a non-human mammal when the composition is brought into close proximity of or into contact with the human body or the body of a non-human mammal, thereby relieving pain in the human body or the body of the non-human mammal.

2. The non-conducting composition of claim 1, wherein the particles have an average diameter of less than about 40 microns.

3. The non-conducting composition of claim 1, wherein the ratio of elemental iron to elemental zinc is between 1000:1 and 1:1000.

4. The non-conducting composition of claim 1, wherein the ratio of elemental iron to elemental aluminum is between 1000:1 and 1:1000.

5. The non-conducting composition of claim 1, wherein the ratio of elemental iron to elemental copper is between 1000:1 and 1:1000.

6. A method of reducing pain in a human or non-human mammal in need thereof, comprising contacting a body surface of the human or non-human mammal near a region having pain with the non-conducting composition of claim 1.

7. The non-conducting composition of claim 1, wherein the composition is flexible, malleable, or rigid.

8. The non-conducting composition of claim 1, wherein the matrix protects the elemental iron, zinc, copper, and aluminum from oxidation.

9. The non-conducting composition of claim 1, wherein the composition is sticky.

10. The non-conducting composition of claim 1, wherein the composition comprises 29.6% by weight of iron, 25.6% by weight of zinc, and up to 10% by weight of aluminum and copper.

11. The non-conducting composition of claim 1, wherein the ratio of total metal particles to the matrix is between 1:100 and 100:1.

12. The non-conducting composition of claim 1, wherein the ratio of total metal particles to the matrix is between 1:10 and 10:1.

13. The non-conducting composition of claim 1, wherein the composition includes not more than 0.01% by weight of oxidized or reduced forms of the elemental iron, zinc, copper, and aluminum.

14. The non-conducting composition of claim 1, wherein the particles are capable of being sieved though a 200 mesh sieve.

15. The non-conducting composition of claim 1, wherein the particles are capable of being sieved though a 325 mesh sieve.

16. The non-conducting composition of claim 1, wherein the matrix comprises wax, and the wax comprises bees wax.

17. The non-conducting composition of claim 1, wherein the matrix comprises silicone.

18. The non-conducting composition of claim 1, wherein a fraction of the particles are separated by the matrix.

19. A non-conducting composition for relieving pain, comprising substantially water-free particles of elemental iron, zinc, copper, and aluminum having an average diameter of less than about 100 microns, distributed within and separated by an insulating matrix substantially free of air pockets and comprising petroleum jelly, lanolin, silicone, wax, or combinations thereof, wherein the composition is non-conducting, wherein the distribution and separation of the particles within the matrix imparts capacitance into the composition, and wherein the capacitance of the composition alters an electrostatic field, an electromagnetic field, or both an electrostatic and an electromagnetic field of the human body when the composition is brought into close proximity of or into contact with the human body, thereby relieving pain in the human body.

20. The non-conducting composition of claim 19, wherein the particles have an average diameter of less than about 40 microns.

21. The non-conducting composition of claim 19, wherein the ratio of elemental iron to elemental zinc is between 1000:1 and 1:1000.

22. The non-conducting composition of claim 19, wherein the ratio of elemental iron to elemental aluminum is between 1000:1 and 1:1000.

23. The non-conducting composition of claim 19, wherein the ratio of elemental iron to elemental copper is between 1000:1 and 1:1000.

24. The non-conducting composition of claim 19, wherein the matrix comprises silicone.

25. The non-conducting composition of claim 19, wherein a fraction of the particles are separated by the matrix.

26. A device for relieving pain in a subject, the device comprising a support, and a non-conducting composition affixed to the support, the non-conducting composition comprising substantially water-free particles of elemental iron, zinc, copper, and aluminum having an average diameter of less than about 100 microns, distributed within and separated by an insulating matrix substantially free of air pockets and comprising petroleum jelly, lanolin, silicone, wax, or combinations thereof, wherein the distribution and separation of the particles within the matrix imparts capacitance into the composition, and wherein the capacitance of the composition alters an electrostatic field, an electromagnetic field, or both an electrostatic and an electromagnetic field of the body of the subject when the composition is brought into close proximity of or into contact with the body, thereby relieving pain in the subject.

27. The device of claim 26, wherein the matrix comprises silicone.

28. The device of claim 26, wherein a fraction of the particles are separated by the matrix.

29. The device of claim 26, wherein the device is a patch.

30. The device of claim 26, wherein the device is shaped to conform and adhere to the surface of a desired body part.

31. A method of reducing pain in a human in need thereof, comprising bringing the composition of claim 19 into proximity with a surface of the human body near a painful region of the body, thereby reducing pain in the painful region.

32. A method of reducing pain in a human in need thereof, comprising contacting the composition of claim 19 with a surface of the human body near a painful region of the body, thereby reducing pain in the painful region.

33. A method of reducing pain in a human in need thereof, comprising contacting the device of claim 26 with a surface of the human body near a painful region of the body, thereby reducing pain in the painful region.

34. The method of claim 33, wherein the device is a patch.

* * * * *